United States Patent [19]
Richards-Kortum et al.

[11] Patent Number: 5,991,653
[45] Date of Patent: Nov. 23, 1999

[54] NEAR-INFRARED RAMAN SPECTROSCOPY FOR IN VITRO AND IN VIVO DETECTION OF CERVICAL PRECANCERS

[75] Inventors: Rebecca Richards-Kortum; Anita Mahadevan-Jansen, both of Austin, Tex.; Nirmala Ramanujam, Philadelphia, Pa.; Michele Follen Mitchell, Houston, Tex.

[73] Assignee: Board of Regents, The University of Texas System, Austin, Tex.

[21] Appl. No.: 08/667,993

[22] Filed: Jun. 19, 1996

Related U.S. Application Data

[63] Continuation-in-part of application No. 08/403,446, Mar. 14, 1995, Pat. No. 5,697,373.

[51] Int. Cl.[6] .................................................. A61B 6/00
[52] U.S. Cl. ........................... 600/475; 436/64; 436/171; 250/339.01; 250/339.06; 250/341.1; 356/301
[58] Field of Search .................................... 600/473, 475; 250/341.1, 339.01, 339.06; 356/301; 436/63, 64, 171

[56] References Cited

U.S. PATENT DOCUMENTS

| | | | |
|---|---|---|---|
| 4,556,057 | 12/1985 | Hiruma et al. | 128/303.1 |
| 4,648,892 | 3/1987 | Kittrell et al. | 65/4.21 |
| 4,675,529 | 6/1987 | Kushida | 250/458.1 |
| 4,755,684 | 7/1988 | Leiner et al. | 250/461.1 |
| 4,786,813 | 11/1988 | Svanberg et al. | 250/461.1 |
| 4,832,483 | 5/1989 | Verma | 356/39 |
| 4,913,142 | 4/1990 | Kittrell et al. | 606/7 |
| 4,930,516 | 6/1990 | Alfano et al. | 128/665 |
| 4,967,745 | 11/1990 | Hayes et al. | 128/303.1 |
| 4,973,848 | 11/1990 | Kolobanov et al. | 250/458.1 |
| 5,003,977 | 4/1991 | Suzuki et al. | 128/633 |
| 5,009,655 | 4/1991 | Daignault, Jr. et al. | 606/7 |
| 5,014,707 | 5/1991 | Schwarz et al. | 128/633 |
| 5,026,368 | 6/1991 | Adair | 606/15 |

(List continued on next page.)

FOREIGN PATENT DOCUMENTS

| | | |
|---|---|---|
| 0 359 433 | 3/1990 | European Pat. Off. |
| 0 608 987 A1 | 8/1994 | European Pat. Off. |
| 0 650 694 | 5/1995 | European Pat. Off. |
| 1151436 | 6/1989 | Japan . |
| WO 88/05908 | 8/1988 | WIPO . |
| WO 90/06718 | 6/1990 | WIPO . |
| WO 90/12536 | 11/1990 | WIPO . |
| WO 92/15008 | 9/1992 | WIPO . |
| WO 93/03672 | 3/1993 | WIPO . |
| WO 94/26168 | 11/1994 | WIPO . |
| WO 95/26673 | 10/1995 | WIPO . |
| WO 96/28084 | 9/1996 | WIPO . |

OTHER PUBLICATIONS

Angel et al., "Computer–Controlled Instrument for the Recovery of a Resonance Raman Spectrum in the Presence of Strong Luminescence," *Anal. Chem.*, 56, 3000–3001, 1984.

Keller et al., "Application of Near–Infrared–Fourier Transform Raman Spectroscopy in Medical Research," *J. Raman Spectrosc.* 25(7–8):663–671, 1994.

Mizumo et al., "Near–Infrared Fourier Transform Raman Spectroscopic Study of Human Brain Tissues and Tumours," *J. Raman Spectrosc.*, 25:25–29 (1994).

(List continued on next page.)

*Primary Examiner*—Ruth S. Smith
*Attorney, Agent, or Firm*—Arnold White & Durkee

[57] ABSTRACT

Early diagnosis of cervical precancer is an important clinical goal. Optical spectroscopy has been suggested as a new technique to overcome limitations of current clinical practice. Herein, NIR Raman spectroscopy is applied to the diagnosis of cervical precancers. Using algorithms based on empirically selected peak intensities, ratios of peak intensities and a combination of Principal Component Analysis (PCA) for data reduction and Fisher Discriminant Analysis (FDA), normal tissues, inflammation and metaplasia were distinguishable from low grade and high grade precancers. The primary contributors to the tissue spectra appear to be collagen, nucleic acids, phospholipids and glucose 1-phosphate. These results suggest that near infrared Raman spectroscopy can be used effectively for cervical precancer diagnosis.

5 Claims, 16 Drawing Sheets

U.S. PATENT DOCUMENTS

| | | | |
|---|---|---|---|
| 5,034,010 | 7/1991 | Kittrell et al. | 606/15 |
| 5,036,853 | 8/1991 | Jeffcoat et al. | 128/634 |
| 5,038,039 | 8/1991 | Wong et al. | 250/339 |
| 5,042,494 | 8/1991 | Alfano | 128/665 |
| 5,046,501 | 9/1991 | Crilly | 128/665 |
| 5,062,431 | 11/1991 | Potter | 128/665 |
| 5,092,331 | 3/1992 | Nakamura et al. | 128/634 |
| 5,104,392 | 4/1992 | Kittrell et al. | 606/15 |
| 5,106,387 | 4/1992 | Kittrell et al. | 606/15 |
| 5,115,137 | 5/1992 | Andersson-Engels et al. | 250/461.2 |
| 5,125,404 | 6/1992 | Kittrell | 128/634 |
| 5,131,398 | 7/1992 | Alfano et al. | 128/665 |
| 5,168,162 | 12/1992 | Oong et al. | 250/339 |
| 5,174,297 | 12/1992 | Dalkuzono | 128/665 |
| 5,192,278 | 3/1993 | Hayes et al. | 606/15 |
| 5,199,431 | 4/1993 | Kittrell et al. | 128/634 |
| 5,201,318 | 4/1993 | Rava et al. | 128/665 |
| 5,251,613 | 10/1993 | Adair | 128/6 |
| 5,261,410 | 11/1993 | Alfano et al. | 128/664 |
| 5,280,788 | 1/1994 | Janes et al. | 128/665 |
| 5,290,275 | 3/1994 | Kittrell et al. | 606/15 |
| 5,293,872 | 3/1994 | Alfano et al. | 128/664 |
| 5,303,026 | 4/1994 | Strobl et al. | 356/318 |
| 5,304,173 | 4/1994 | Kittrell et al. | 606/15 |
| 5,318,023 | 6/1994 | Vari et al. | 128/633 |
| 5,318,024 | 6/1994 | Kittrell et al. | 128/634 |
| 5,345,941 | 9/1994 | Rava et al. | 128/665 |
| 5,348,003 | 9/1994 | Caro | 128/633 |
| 5,348,018 | 9/1994 | Alfano et al. | 128/665 |
| 5,408,996 | 4/1995 | Salb | 128/633 |
| 5,419,323 | 5/1995 | Kittrell et al. | 128/653.1 |
| 5,421,337 | 6/1995 | Richards-Kortum et al. | 128/665 |
| 5,421,339 | 6/1995 | Ramanujam et al. | 128/665 |
| 5,421,346 | 6/1995 | Sanyal | 128/750 |
| 5,450,857 | 9/1995 | Garfield et al. | 128/778 |
| 5,452,723 | 9/1995 | Wu et al. | 128/664 |
| 5,467,767 | 11/1995 | Alfano et al. | 128/665 |
| 5,507,287 | 4/1996 | Palcic et al. | 128/633 |
| 5,552,134 | 9/1996 | Morgan et al. | 424/9.61 |
| 5,596,992 | 1/1997 | Haaland et al. | 600/473 |

OTHER PUBLICATIONS

Van Duyne et al., "Mode–Locked Laser Raman Spectroscopy—A New Technique for the Rejection of Interfering Background Luminescence Signals," *Anal. Chem.*, 46, 213–222, 1974.

Yu et al., "Laser Raman Spectroscopy of the Lens In–Situ Measured in an Anesthesized Rabbit," *Curr. Eye Res.*, 1(10):615–618, 1982. Abstract only.

Alfano et al., "Optical Spectroscopic Diagnosis of Cancer in Normal Breast Tissues," *J. Opt. Soc. Am. B.*, 6:1015–1023, May 1989.

Alfano et al., "Human Breast Tissues Studied by IR Fourier Transform Raman Spectroscopy," *Lasers in the Life Sciences*, 4(1):23–28, 1991.

Baraga et al., "In situ Optical Histochemistry of Human Artery Using Near Infrared Fourier Transform Raman Spectroscopy," *Proc. Natl. Acad. Sci.*, 89:3473–3477, 1992.

Bot et al, "Raman Microspectroscopy of Fixed Rabbit and Human Lenses and Lens Slices: New Potentials," *Exp. Eye Res.*, 49:161–169, 1989.

Brennan et al., "In situ Histochemical Analysis of Human Coronary Arteries by Raman Spectroscopy Compared with Biochemical Assay," In *Advances in Fluorescence Sensing Technology*, vol. II, ed. J.R. Lakowicz, *SPIE Proceedings*, 2388:105–109, 1995.

Clarke et al., "Laser Raman Spectroscopy of Calcified Atherosclerotic Lesions in Cardiovascular Tissue," *Applied Optics*, 26(16):3175–3177, 1987.

Dillon and. Goldstein, *Principal Components Analysis, In: Multivariate Analysis, Methods and Applications*, Chapter 2:23–392, 1984.

Feld et al., "Detection and Characterization of Human Tissue Lesions with Near Infrared Raman Spectroscopy," *SPIE*, 2388:99–104, 1995.

Frank et al., "Characterization of Human Breast Biopsy Specimens with Near–IR Raman Spectroscopy," *Analytical Chemistry*, 66(3)19–326, 1994.

Frank et al., "Raman Spectroscopy of Normal and Diseased Human Breast Tissues," *Analytical Chemistry*, 67(5):777–783, 1995.

Funfschilling and Williams, "CW Laser Wavelength Modulation in Raman and Site Selection Fluorescence Spectroscopy," *Applied Spectroscopy*, 30(4):443–446, 1976.

Kapadia et al., "Laser–Induced Spectroscopy of Human Colonic Mucosa: Detection of Adenomatous Transformation," *Gastroenterology*, 99:150–157, 1990.

Kramer et al., "Spectral Diagnosis of Human Coronary Artery: A Clinical System for Real Time Analysis," *SPIE*, 2395:376–382, 1995.

Lewis et al., "Raman Spectrometry and Neural Networks for the Classification of Wood Types—1," *Spectrochimica Acta*, 50A(11):1943–1958, 1994.

Liu et al., "Near–IR Fourier Transform Raman Spectroscopy of Norman and Atherosclerotic Human Aorta," *Lasers in the Life Sciences*, 4(3):257–264, 1992.

Liu et al., "Raman, Fluorescence, and Time–Resolved Light Scattering as Optical Diagnostic Techniques to Separate Diseased and Normal Biomedical Media," *Journal of Photochemistry & Photobiology*, 16(2):187–209, 1992. Abstract only.

Liu et al., "Raman, Fluorescence, and Time–Resolved Light Scattering as Opitical Diagnostic Techniques to Separate Diseased and Normal Biomedical Media," *J Photochem. Photobiol. B: Biol.*, 16:187–209, 1992.

Mahadevan et al, "Optical Techniques for the Diagnosis of Cervical Precancers: A Comparison of Raman and Fluorescence Spectroscopies," *SPIE*, 2388:110–120, 1995.

Manoharan et al., "Raman Spectroscopy for Cancer Detection: Instrument Development and Tissue Diagnosis," *SPIE*, 2328, 128–132, 1994.

Manoharan et al., "Ultraviolet Resonance Raman Spectroscopy for Detection of Colon Cancer," *Lasers in the Life Sciences*, 6(4):217–227, 1995.

Mosier–Boss et al., "Fluorescence Rejection in Raman Spectroscopy by Sifted–Spectra, Edge Detection, and FFT Filtering Techniques," *Applied Spectroscopy*, 49(5):630–638, 1995.

Myric and Angel, "Elimination of Background in Fiber–Optic Raman Measurements," *Applied Spectroscopy*, 44(4):565–570, 1990.

Myrick et al., "Comparison of Some Fiber Optic Configurations for Measurement of Luminescence and Raman Scattering," *Applied Optics*, s29(9):1333–1344, 1990.

Nie et al., "Applications of Near–Infrared Fourier Transform Raman Spectroscopy in Biology and Medicine," *Spectroscopy*, 5(7):24–32 (1990).

Ozaki, "Medical Application of Raman Spectroscopy," *Applied Spectroscopy Reviews*, 24(3 & 4):259–312, 1988.

Puppels et al., "Laser Irradiation and Raman Spectroscopy of Single Living Cells and Chromosomes: Sample Degradation Occurs With 514.5 nm but Not With 660 nm Laser Light," *Experimental Cell Research*, 195(2):361–367 (1991).

Puppels et al., "Raman Microspectroscopic Approach to the Study of Human Granulocytes," *Biophys. J.*, 60:1046–1056, 1991.

Redd et al., "Raman Spectroscopic Characterization of Human Breast Tissues: Implications for Breast Cancer Diagnosis," *Applied Spectroscopy*, 47(6):787–791, 1993.

Richards–Kortum et al., "Spectroscopic Diagnosis of Colonic Dysplasia," *Photochemistry and Photobiology*, 53:777–786, 1991.

Schrader et al., "NIR FT Raman Spectroscopy in Medical Diagnosis," *Journal of Molecular Structure*, 348:293–296, 1995.

Schwab and McCreery, "Versatile, Efficient Raman Sampling with Fiber Optics," *Anal. Chem.*, 56:2199–2204, 1984.

Shreve et al., "Effective Rejection of Fluorescence Interference in Raman Spectroscopy Using a Shifted Excitation Difference Technique," *Applied Spectroscopy*, 46(4):707–711, 1992.

Small et al., "Strategies for Coupling Digital Filtering with Partial Least–Squares Regression: Application to the Determination of Glucose in Plasma by Fourier Transform Near–Infrared Spectroscopy," *Anal. Chem.*, 65:3279–3289, 1993.

Walpole and R. Myers, *Tests of Hypotheses, In: Probability and Statistics for Engineers and Scientists, 2nd Ed.*, Chapter 7:v,238–259, 1978.

Williams and Barry, "Comparison of Fourier Transform Raman Spectra of Mammalian and Reptilian Skin," *Analyst*, 119:563–566, 1994.

Williams et al., "A Critical Comparison of Some Raman Spectroscopic Techniques for Studies of Human Stratum Corneum," *Pharmaceutical Research*, 10(11):1642–1647, 1993.

Wong et al., "Infrared Spectroscopy of Exfoliated Human Cervical Cells: Evidence of Extensive Structural Changes During Carcinogensis," *Proc. Natl. Acad. Sci. USA*, 88:10988–10992, 1991.

Yu et al., "Disulfide Bond Formation in the Eye Lens," *Proc. Natl. Acad. Sci. USA*, 82:7965–7968, 1985.

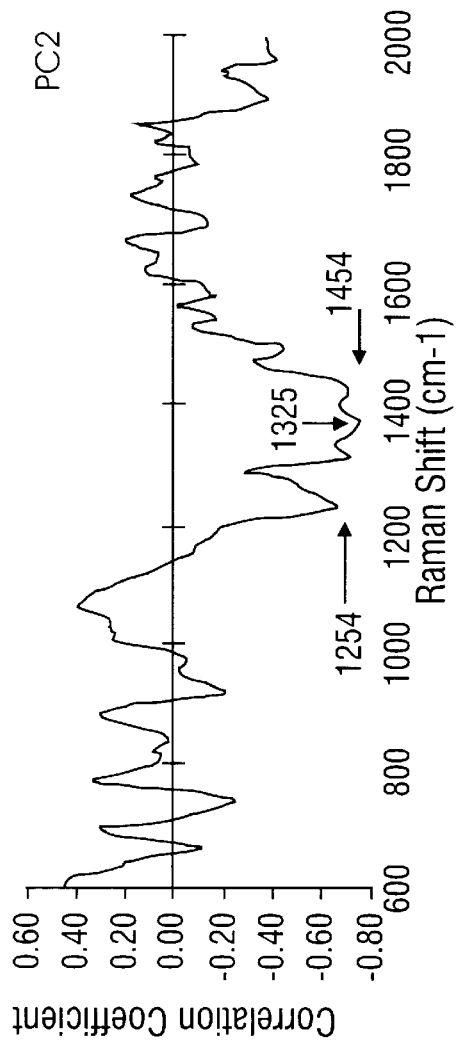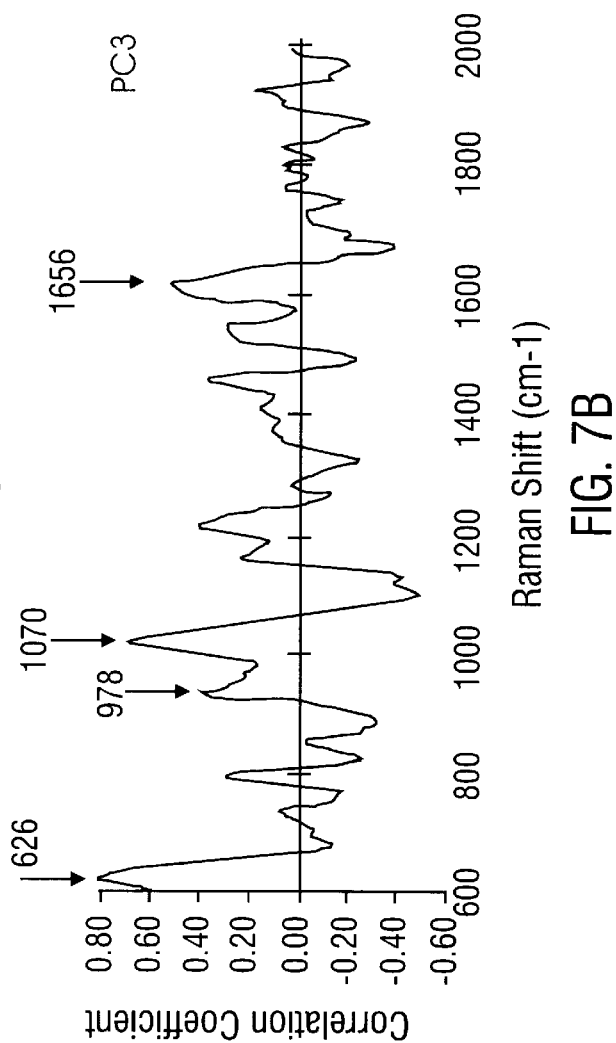
FIG. 7A
FIG. 7B

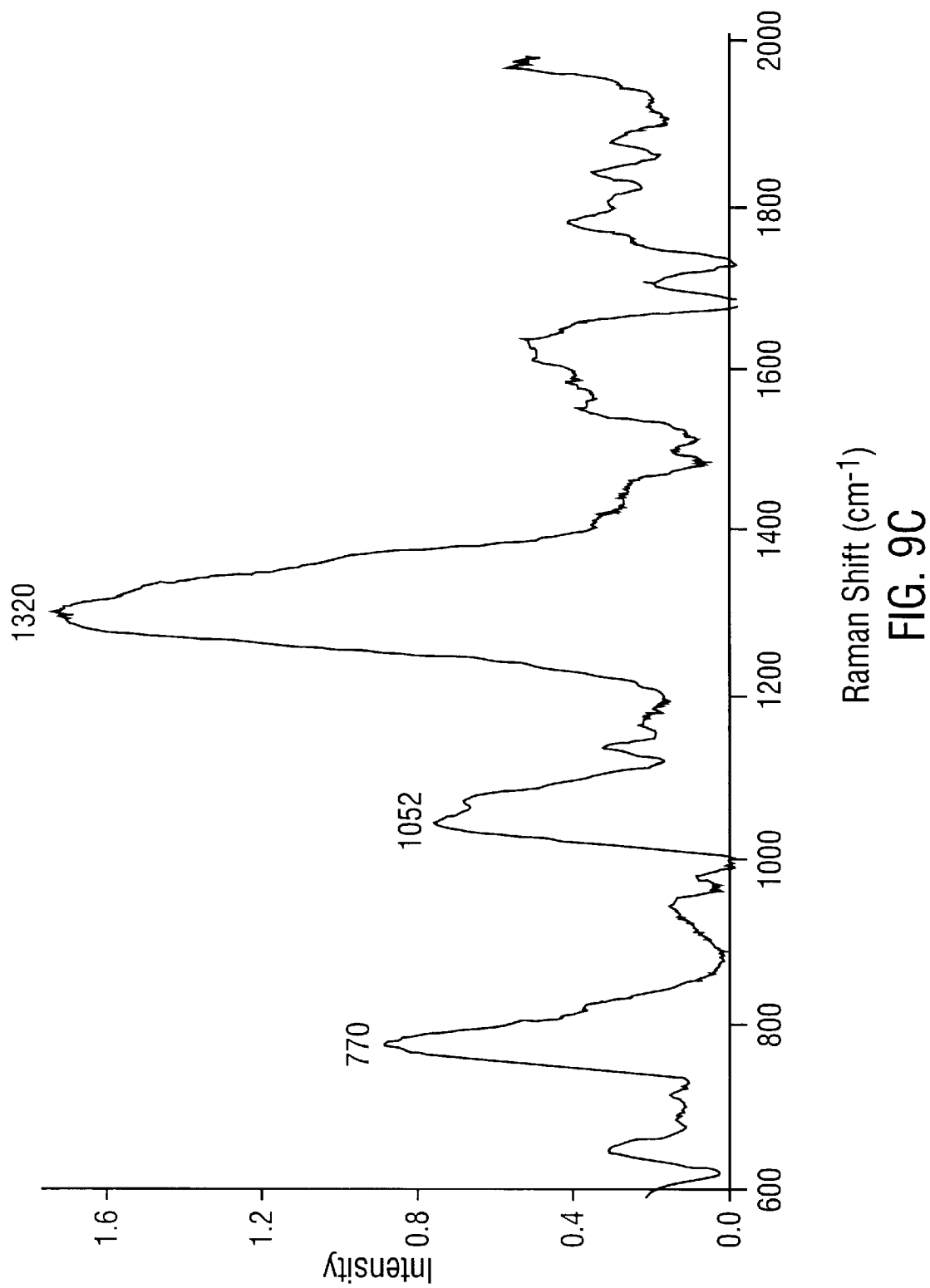

NEAR-INFRARED RAMAN SPECTROSCOPY FOR IN VITRO AND IN VIVO DETECTION OF CERVICAL PRECANCERS

This application is a continuation-in-part of U.S. application Ser. No. 08/403,446, filed on Mar. 14, 1995 now U.S. Pat. No. 5,697,373.

BACKGROUND OF THE INVENTION

I. Field of the Invention

The invention relates to optical methods and apparatus for the diagnosis of cervical precancers.

II. Related Art

Cervical cancer is the second most common malignancy among women worldwide. In 1995, it was estimated that 4,800 deaths will occur in the United States alone from this disease and 15,800 new cases of invasive cervical cancer will be diagnosed. Although early detection of cervical precancer has played a central role in reducing the mortality associated with this disease over the last 50 years (G. H, Anderson, British Med J, 296, 975 (1988), which is hereby incorporated by reference, the incidence of pre-invasive squamous carcinoma of the cervix has risen dramatically, especially among women under the age of 35 (T, C. Wright, R. J., A. Ferenczy, "Cervical Intraepithelial Neoplasia" in *Blaustein's Pathology of the Female Genital Traci*, (Springer-Verlag, New York, 1994), p. 156), which is hereby incorporated by reference. Existing screening and detection techniques, the Pap smear and colposcopy, have several deficiencies that prevent efficient management of an otherwise controllable disease. The primary screening tool is the Pap smear, which has a high false negative error rate of 15–40% due to sampling and reading errors (L. G. Koss, J Am Med Assoc, 261, 737 (1989), which is hereby incorporated by reference. Colposcopy, which usually follows an abnormal Pap smear, requires extensive training and its accuracy is variable and limited even in the hands of expert practitioners (M. F. Mitchell, "Diseases of the Female Lower Genital Tract" in *Operative Gynecology*, (W. B. Saunders, Philadelphia, 1993), p 231), which is hereby incorporated by reference. The mortality of cervical cancer among women under 50 years increased by 3% between 1986 and 1990, all preventable, and this trend may continue unless further improvements are made in current detection techniques (B. A. Miller, L. A. G. Flies, B. F. Hankey, Kosary, A. Harras, S. S. Devesa, B. K. Edwards, *Seer Cancer Statistics Review 1973–1990*, (US Department of Health and Human Services, Bethesda, 1993), p. v.1.), which is hereby incorporated by reference.

Recently, fluorescence, infrared absorption and Raman spectroscopes have been proposed for cancer and precancer screening and diagnosis (R. R. Alfano, G. C. Tang, A. Pradhan, W. Lam, D. S. C. Choy, A. Opher, IEEE Journal of Quantum Electronics, QE-23, 1806 (1987).; J. Hung, S. Lam, J. C. LeRiche, B. Palcic, Lasers Surg Med, 11, 99 (1991); R. M. Cothren, R. Richards-Kottum, M. V. Sivak, M. Fitzmaurice, R. P. Rava, G. A. Boyce, G. B. Hayes, M. Doxtader, R. Blackman, T. Ivanc, M. S. Feld, R. E. Petras, Gastrointest Endoscop, 36, 105 (1990); W. S. Glassman, C. H. Liu, G. C. Tang, S. Lubicz, R. R. Alfano, Lasers in Life Sciences, 5, 49 (1992); W. Lohmann, J. Mußmann, C. Lothmann, W. Kunzel, Euro Jour Obstet Gynecol Reprod Biol, 31, 249 (1989); N. Ramanujam, M. F. Mitchell, A. Mahadevan, S. Thomsen, R. Richards-Kortum, Proc Natl Acad Sc, 91. 10193 (1994);, D. C. B. Redd, Z. C. Feng, K. T. Yue, T. S. Gansler, Appl Spectr, 47, 787 (1993), which are all hereby incorporated by reference. Many groups have successfully demonstrated the potential of spectroscopic techniques to improve diagnosis in various organ systems (M. Motamedi, R. J. Erckens, M. J. Goetz Jr., J. P. Wicksted, G. L. Cote, W. F. March, SPIE, 2388, (1995); Y. Ozaki, A. Mizuno, SPIE, 1403, (1990); C. H. Lui, B. B. Das, W. L. Sha Glassman, G. C. Tang, K. M. Yoo, H. R. Zhu, D. L. Akins, S. S. Lubicz, J. Cleary, R. Prudente, E. Cellmer, A. Caron, R. R. Alfano, J Photochem Photobiol B: Biol, 16, 187 (1992); M. S. Feld, J. F. Brennan III, A. Berger, R. Manoharn, Y. Wang, SPIE, 2388, 99 (1995); R. R. Alfano, C. H. Lui, W. L. Sha, H. R. Zhu, D. L. Akins, J. Cleary, R. Prudente, E. Cellmer, Lasers in Life Sc, 4, 23 (1991); J. F. Brennan III, T. J. Fomer, Y. Wang, A. M. Tercyak, R. S. Lees, R. R. Dasari, J. R. Kramer, M. S. Feld, SPIE, 2388, 105 (1995); J. J. Baraga, M. S. Feld, R. P. Rava, Appl Spectr, 46, 187 (1992)., Y. Wang, R. L. McCreery, Anal Chem, 61, 2647 (1989)., A. Mahadevan, N. Ramanujam, M. F. Mitchell, A. Malpica, S. Thomsen, R. Richards-Kortum, SPIE, 2388, 110 (1995), all of which are hereby incorporated by reference. Intrinsic tissue fluorescence has been used to differentiate normal and abnormal tissues in the human breast and lung, bronchus and gastrointestinal tract. Fluorescence spectroscopy has been shown to be a promising technique for the clinical diagnosis of cervical precancer and extensive clinical trials show that its performance is similar to that of colposcopy in expert hands.

Multivariate statistical techniques have been used to diagnose cervical precancers based on fluorescence spectra acquired at multiple excitation wavelengths. A prospective evaluation of the algorithms indicates that at 337 nm excitation, normal tissues can be differentiated from precancers with a sensitivity of 91% and specificity of 82%. In addition, spectra at 460 nm excitation can differentiate normal cervix and precancers with a sensitivity and specificity of 91% and 75.5%, respectively, as well as differentiate high grade and low grade precancers with a sensitivity and specificity of 80% and 76%, respectively.

To further improve the diagnostic capability of spectroscopy for detection of cervical precancers, Raman spectroscopy has been considered. In comparison with fluorescence, Raman signals are weak and require sensitive instrumentation for detection. However, only a limited number of biological molecules contribute to tissue fluorescence, most with broadband emission. Many more molecules are Raman-active, with fingerprint spectra providing molecular specific information that can be applied to diagnose diseased tissue. As a result, in recent years, several groups have studied the potential of Raman spectroscopy for disease detection. Alfano et al. have used Fourier Transform Raman spectroscopy to detect gynecologic malignancies. Several groups have applied Raman spectroscopy to breast cancer detection. Feld et al. have demonstrated the use of NIR and UV resonance Raman spectroscopy for identification of colon cancer and atherosclerosis.

Nonetheless, automated diagnostic methods with improved diagnostic capabilities are needed to allow faster, more effective patient management and potentially further reduce mortality.

SUMMARY OF THE INVENTION

The present invention demonstrates that Raman spectroscopy can be applied, both in vitro and in vivo, to the diagnosis of cervical tissue abnormalities including the clinical detection of cervical precancer.

There is provided a method of detecting tissue abnormality in a tissue sample comprising the steps of (i) providing a tissue sample; (ii) illuminating said sample with an electromagnetic radiation wavelength from the near infrared to produce a Raman spectrum shifted from the illumination wavelength; (iii) detecting a plurality of emission frequencies of said spectrum; and (iv) establishing from said emission frequencies a probability that said sample is abnormal. The illumination wavelength may be about 700–850 nm, and more specifically about 789 nm.

The establishing step may comprise measuring said emission frequencies relative to the illuminating electromagnetic radiation wavelength. The emission frequencies are advantageously shifted about 626, 818, 978, 1070, 1175, 1246, 1330, 1454 and 1656 $cm^{-1}$ from the illumination wavelength. For example, emission frequencies shifted about 1070 $cm^{-1}$ and about 1656 $cm^{-1}$ from the illumination wavelength distinguish precancers and non-precancers. Emission frequencies shifted about 1330 and 1656 $cm^{-1}$ from the illumination wavelength distinguish precancer and non-precancers. Emission frequencies shifted about 1454 and 1656 $cm^{-1}$ from the illumination wavelength distinguish low grade precancerous and high grade precancerous.

The method may comprise illumination in vitro or in vivo. For in vitro, the providing step may comprise obtaining a sample by biopsy. In this case, the providing step may further comprise generating a monolayer cell touch preparation or a pellet and ethanol fixation of said sample.

There also is provided a method of developing a mathematical model for predicting testing abnormality in a tissue sample comprising the steps of (i) providing a plurality of tissue samples; (ii) illuminating said samples with an electromagnetic radiation wavelength from the near infrared to produce a Raman spectrum for each of said samples shifted from the illumination wavelength; (iii) detecting a plurality of emission frequencies of said spectra; (iv) forming a set of principal components from preprocessed data, said principal components being defined as providing statistically significant differences between normal tissue and various forms of abnormal tissue; and (v) subjecting said principal components to logistic discrimination to develop a relevant mathematical model. The illumination wavelength advantageously is about 789 nm.

In yet another embodiment, the present invention provides a method of Raman spectroscopy coupled with illuminating the tissue sample with a plurality of electromagnetic radiation wavelengths sufficient to generate a plurality of fluorescence intensity spectra and detecting said a fluorescence intensity spectra therefrom. The method advantageously utilizes a plurality of electromagnetic radiation wavelengths at about 337 nm, about 380 nm and about 460 nm. More particularly, the fluorescent wavelengths are in the ranges of 317–357 nm, 360–400 mn and 440–480 nm. This method may further comprise the step of preprocessing fluorescent data at the emission wavelengths to reduce inter-sample and intra-sample variation and, even further, may comprise the step of forming a set of principal components from said preprocessed fluorescent data, said principal components being defined as providing statistically significant differences between normal tissues and various forms of abnormal tissue.

In still yet another embodiment, there is provided a method of detecting tissue abnormality in a tissue sample comprising the steps of (i) providing said sample; (ii) illuminating said sample with an electromagnetic radiation wavelength from the near infrared to produce a Raman spectrum shifted from the illumination wavelength; (iii) detecting at least one emission frequency of said spectrum that is associated with compound selected from the group consisting of collagen, phopholipids and glucose-1-phosphate; and (iv) establishing from said emission frequency a probability that said sample is abnormal. The emission frequency may be associated with collagen, phospholipids or glucose-1-phosphate.

In still yet another embodiment, there is provided a method of detecting tissue abnormality in a subject in vivo comprising the steps of (i) illuminating a tissue sample with an electromagnetic radiation wavelength from the near infrared to produce a Raman spectrum shifted from the illumination wavelength; (ii) detecting a plurality of emission frequencies of said spectrum; and (iii) establishing from said emission frequencies a probability that said sample is abnormal. The illumination wavelength is advantageously about 700–850 nm.

In still yet another embodiment, there is provided a method of diagnosing cervical precancer in a patient comprising the steps of (i) illuminating said sample with an electromagnetic radiation wavelength from the near infrared to produce a Raman spectrum shifted from the illumination wavelength; (ii) detecting a plurality of emission frequencies of said spectrum; (iii) comparing said plurality of emission frequencies from said patient with known emission frequencies for normal tissue; and (iv) making a diagnostic prediction of the condition of said cervical tissue.

The apparatus of the present invention for obtaining Raman spectral data from a tissue sample includes, a light source for illuminating the tissue sample with at least one wavelength in the near infrared, a detector for detecting a Raman emission spectrum emitted from said tissue sample; and a programmed computer in operable connection with the detector, for processing said Raman emission spectrum according to a predetermined algorithm so as to predict the condition of the tissue sample. The light source may be a laser, and the illumination wavelength may be about 789 nm.

The apparatus may further include a device for holding the tissue sample in operable relation relative to the light source and the detector.

The predetermined algorithm may include principal components that predict statistically relevant differences between emission frequencies of normal and abnormal tissues for the illumination wavelength. Finally, the abnormal tissues may be inflamed tissue, metaplastic tissue, low grade SIL and high grade SIL.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specific embodiments presented herein.

(FIG. 4A) Scatter plot of normalized intensity at 1070 $cm^{-1}$ with respect to sample type. The decision line differentiates between SILs and non-SILs with a sensitivity and specificity of 82% and 96% and (FIG. 4B) scatter plot of normalized intensity at 1656 $cm^{-1}$ with respect to sample type. Line 1 separates SILs and non-SILs with a sensitivity and specificity of 91% and 88%. Line 2 separates high grade and low grade SILs with a sensitivity and specificity of 86% and 100%.

(FIG. 5A) Scatter plot of the ratio of unnormalized intensities at 1656 $cm^{-1}$ and 1330 $cm^{-1}$ with respect to sample type. The decision line separates SILs and non-SILs with a sensitivity and specificity of 82% and 80%. (FIG. 5B) Scatter plot of the ratio of unnormalized intensities at 1656 $cm^{-1}$ and 1454 $cm^{-1}$ with respect to sample type for samples classified as SILs in FIG. 6. The decision line separates high grade and low grade SILs with a sensitivity and specificity of 100%

FIGS. 9A, 9B, 9C and 9D: Chromophore Raman spectra measured using setup in FIG. 1 of (FIG. 9A) collagen in its pure form, (FIG. 9B) glucose phosphate in its pure form, (FIG. 9C) DNA in its pure form and (FIG. 9D) phosphatidylcholine (a phospholipid) in its pure form.

DETAILED DESCRIPTION

I. The Present Invention

The goal of this study was to characterize the NIR Raman spectra of cervical tissues and assess the feasibility of using Raman spectroscopy for detection of cervical precancer. Two different methods of algorithm development for tissue differentiation were considered. The first used empirically selected peak intensities and ratios of peak intensities to differentiate precancers from other tissue categories and differentially diagnose high grade and low grade precancers. A second, multivariate statistical method was used to differentiate precancers from other tissues and was based on principal component analysis and Fisher discriminant analysis. The multivariate algorithm was first developed using the entire Raman spectrum. Component loadings were then used to select those spectral frequencies highly correlated to diagnosis. Results indicate that accurate separation of precancers and non-precancers can be achieved based on Raman intensities at a small number of frequencies. An attempt was made to identify the Raman peaks observed in the tissue spectra and correlate the morphological and molecular changes that occur with cervical precancer to the spectral changes observed in normal and precancerous tissue. Chromophore spectra were measured and compared qualitatively to tentatively identify the different chromophores that contribute to the Raman spectra of normal and precancerous cervix.

Figure 2:
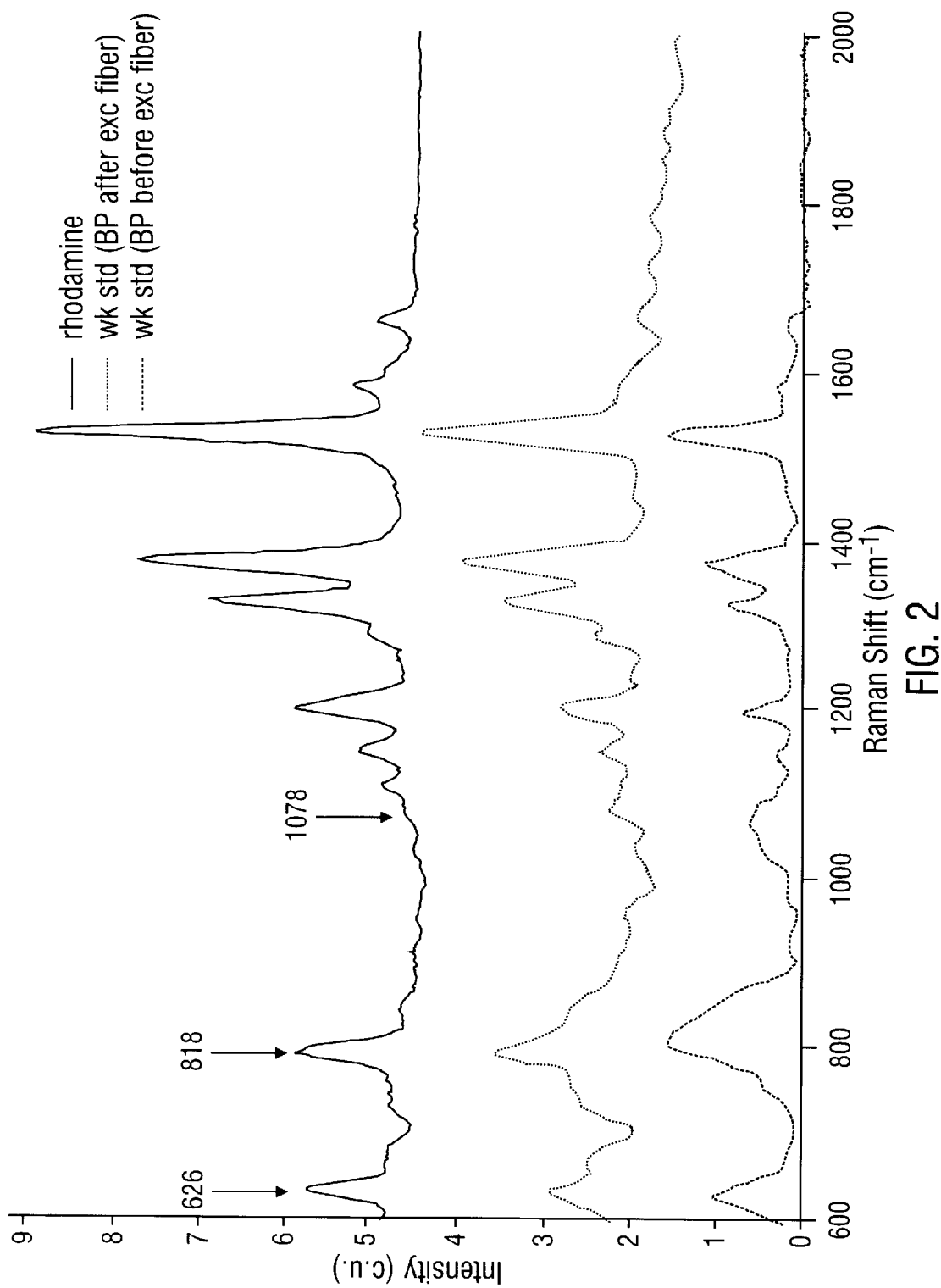
FIG. 2: (top) Raman spectrum of pure rhodamine 6G; (middle) difference of Raman spectra of KIR and potassium iodide with the bandpass filter before the excitation fiber; (bottom) difference spectrum with bandpass filter after the excitation fiber.

This study shows that near infrared Raman spectroscopy is a promising technique for identification of cervical precancer. Despite substantial patient-to-patient variability in the intensity of Raman peaks, accurate diagnostic algorithms for identification of SILs and differentiation of high grade and low grade SILs were developed based on intensities at a few frequencies, indicating that the shape of the bands are not critical for diagnosis. It further was shown that the multivariate technique accounts for the inter-patient variability that limits performance of empirical methods by excluding those principal components which describe inter-patient variations. It should be noted that all tissue spectra were analyzed together despite the differences in the experimental setup used for some samples. Although FIGS. 2 and 3 show the differences in the spectral characteristics due to silica Raman, it is believed that principal component analysis also accounts for variations in Raman spectra due to system alterations. Study of the principal components not used in the diagnostic algorithm shows that principal component 1 (PC1) separates the first 5 pairs of samples from the remaining samples, indicating that PC1 accounts for the differences in tissue spectra due to silica Raman. Thus, multivariate statistical analysis allows objective diagnosis by retaining only those principal components which describe inter-category differences.

The diagnostic ability of NIR Raman spectroscopy shows some important differences from, and advantages relative to, other optical techniques proposed for tissue diagnosis, such as fluorescence spectroscopy. Studies indicate that fluorescence based algorithms that use multivariate statistical techniques can successfully diagnose SILs from normal tissues at multiple excitation wavelengths. Unbiased estimates of the multivariate fluorescence and Raman based algorithms can be compared to evaluate the relative effectiveness of the techniques. Fluorescence can differentiate SILs and normal tissues based on spectra at 337 and 460 nm excitation with a sensitivity and specificity of 91% and 79% (±3%). However, samples with benign lesions such as inflammation and metaplasia are sometimes diagnosed falsely as SILs at both wavelengths. Fluorescence can also differentiate high grade and low grade SILs at 460 nm excitation in an unbiased manner with a sensitivity and specificity of 80% and 76%. Raman spectroscopy can differentiate SILs and normal tissues in an unbiased manner with similar sensitivity and specificity. However, in this study of 36 samples, Raman spectroscopy correctly separated inflammation and metaplasia from SILs, as would be important in a clinical setting. This supports the notion that increased penetration depth of NIR excitation allows recognition of inflammation and metaplasia; benign processes that primarily manifest themselves in the stroma. It is concluded that NIR Raman spectroscopy, alone or in conjunction with fluorescence spectroscopy, is a promising new technique which may yield an effective and clinically useful diagnostic scheme for cervical precancer.

II. Multi-Variate Statistical Method Development

The five primary steps involved in the multivariate statistical method of the present invention are (i) data preprocessing, (ii) dimension reduction using principal component analysis, (iii) selection of the diagnostically most useful principal components using a two-sided unpaired t-test, (iv) development of a classification algorithm using Fisher Discriminant Analysis and (v) an unbiased evaluation of algorithm performance using cross validation. These five individual steps of the multivariate statistical method are presented below in more detail.

(i) Data Preprocessing:

The observed noise was established to be approximately gaussian, indicating that simple filtering techniques would be effective in smoothing the curves. Optimal results were obtained when the spectrum was convolved with a gaussian whose full width half maximum was equal to the resolution of the system. The technique discards any signal bandwidth less than the resolution of the system. The filtered signal still contains both fluorescence and Raman signals. A fifth degree polynomial was found to be optimal in this study. The best fit polynomial was then subtracted from the spectrum to yield Raman signal alone. Each tissue spectrum was similarly preprocessed.

(ii) Principal Component Analysis:

Principal component analysis (PCA) is a linear model which transforms the original variables of an emission spectrum into a smaller set of linear combinations of the original variables called principal components that account for most of the variance of the original data set. Principal component analysis is described in Dillon W. R., Goldstein M., *Multivariate Analysis: Methods and Applications*, John Wiley and Sons, 1984, pp. 23–52 R. W. Dillon, M. Goldstein, *Multivariate Analysis: Methods and Applications*, (John Wiley and Sons, New York, 1984), which is hereby incorporated by reference, the disclosure of which is expressly incorporated herein by reference. While PCA may not provide direct insight to the morphologic and biochemical basis of tissue spectra, it provides a novel approach of condensing all the spectral information into a few manageable components, with minimal information loss. Furthermore, each principal component can be easily related to the original emission spectrum, thus providing insight into diagnostically useful emission variables.

Prior to PCA, a data matrix is created where each row of the matrix contains the preprocessed spectrum of a sample and each column contains the preprocessed intensity at each emission wavelength. The data matrix D (r×c), consisting of r rows (corresponding to r total samples from all patients in the training set) and c columns (corresponding to intensity at c emission wavelengths) can be written as:

$$D = \begin{pmatrix} D_{11} & D_{12} & \dots & D_{1c} \\ D_{21} & D_{22} & \dots & D_{2c} \\ & & & \\ D_{r1} & D_{r2} & \dots & D_{rc} \end{pmatrix} \qquad 1$$

The first step in PCA is to calculate the covariance matrix, Z. First, each column of the preprocessed data matrix D is mean-scaled. The mean-scaled preprocessed data matrix, $D_m$ is then multiplied by its transpose and each element of the resulting square matrix is divided by (r−1), where r is the total number of samples. The equation for calculating Z is defined as:

$$Z = \frac{1}{r-1}(D_m/D_m) \qquad 2$$

The square covariance matrix, Z (c×c) is decomposed into its respective eigenvalues and eigenvectors. Because of experimental error, the total number of eigenvalues will always equal the total number of columns (c) in the data matrix D assuming that c<r. The goal is to select n<c eigenvalues that can describe most of the variance of the original data matrix to within experimental error. The variance, V accounted for by the first n eigenvalues can be calculated as follows:

$$V = 100 \left( \frac{\sum_{j=1}^{n} \lambda_j}{\sum_{j=1}^{c} \lambda_j} \right) \qquad 3$$

The criterion used in this analysis was to retain the first n eigenvalues and corresponding eigenvectors that account for 99% of the variance in the original data set.

Next, the principal component score matrix can be calculated according to the following equation:

$$R=DC \qquad 4$$

where, D (r×c) is the preprocessed data matrix and C (c×n) is a matrix whose columns contain the n eigenvectors which correspond to the first n eigenvalues. Each row of the score matrix R (r×c) corresponds to the principal component scores of a sample and each column corresponds to a principal component. The principal components are mutually orthogonal to each other.

Finally, the component loading is calculated for each principal component. The component loading represents the correlation between the principal component and the variables of the original emission spectrum. The component loading can be calculated as shown below:

$$CL_{ij} = \frac{C_{ij}}{\sqrt{S_{ii}}} \sqrt{\lambda_j} \qquad 5$$

where, $CL_{ij}$ represents the correlation between the ith variable (preprocessed intensity at ith emission wavelength) and the jth principal component. $C_{ij}$ is the ith component of the jth eigenvector, $\lambda_j$ is the jth eigenvalue and $S_{ii}$ is the variance of the ith variable.

Principal component analysis was performed on each type of preprocessed data matrix, described above. Eigenvalues accounting for 99% of the variance in the original preprocessed data set were retained. The corresponding eigenvectors were then multiplied by the original data matrix to obtain the principal component score matrix R.

(iii) Student's T-Test:

Average values of principal component scores were calculated for each histo-pathologic tissue category for each principal component obtained from the preprocessed data matrix. A two-sided unpaired student's t-test was employed to determine the diagnostic contribution of each principal component. Such a test is disclosed in Devore J. L., *Probability and Statistics for Engineering and the Sciences*, Brooks/Cole, 1992, and in Walpole R. E., Myers R. H., *Probability and Statistics for Engineers and Scientists*, Macmillan Publishing Co., 1978, Chapter 7, the disclosures of which are expressly incorporated herein by reference. The hypothesis that the means of the principal component scores of two tissue categories are different were tested for 1) normal squamous epithelia and SILs, 2) columnar normal epithelia and SILs and 3) inflammation and SILs. The t-test was extended a step further to determine if there are any statistically significant differences between the means of the principal component scores of high grade SILs and low grade SILs. Principal components for which the hypothesis stated above were true below the 0.05 level of significance were retained for further analysis.

(iv) Logistic Discrimination:

Logistic discriminant analysis is a statistical technique that can be used to develop diagnostic methods based on posterior probabilities, overcoming the drawback of the binary decision scheme employed in the two-stage method. This statistical classification method is based on Bayes theorem and can be used to calculate the posterior probability that an unknown sample belongs to each of the possible tissue categories identified. Logistic discrimination is discussed in Albert A., Harris E. K., *Multivariate Interpretation of Clinical Laboratory Data*, Marcel Dekker, 1987, the disclosure of which is expressly incorporated herein by reference. Classifying the unknown sample into the tissue category for which its posterior probability is highest results in a classification scheme that minimizes the rate of misclassification.

For two diagnostic categories, $G_1$ and $G_2$, the posterior probability of being a member of $G_1$, given measurement x, according to Bayes theorem is:

$$P(G_1 \mid X) = \frac{P(x \mid G_1)P(G_1)C(2 \mid 1)}{P(x \mid G_1)P(G_1)C(2 \mid 1) + P(x \mid G_2)P(G_2)C(1 \mid 2)} \quad 6$$

where $P(x \mid G_i)$ is the conditional joint probability that a tissue sample of type i will have principal component score x, and $P(G_i)$ is the prior probability of finding tissue type i in the sample population. $C(j \mid i)$ is the cost of misclassifying a sample into group j when the actual membership is group i.

The prior probability $P(G_i)$ is an estimate of the likelihood that a sample of type i belongs to a particular group when no information about it is available. If the sample is considered representative of the population, the observed proportions of cases in each group can serve as estimates of the prior probabilities. In a clinical setting, either historical incidence figures appropriate for the patient population can be used to generate prior probabilities, or the practitioner's colposcopic assessment of the likelihood of precancer can be used to estimate prior probabilities.

The conditional probabilities can be developed from the probability distributions of the n principal component scores for each tissue type, i. The probability distributions can be modeled using the gamma function, which is characterized by two parameters, alpha and beta, which are related to the mean and standard deviation of the data set. The Gamma function is typically used to model skewed distributions and is defined below:

$$f(x; \alpha, \beta) = \frac{1}{\beta^\alpha \Gamma(\alpha)} x^{\alpha-1} e^{-x/\beta} \quad 7$$

The gamma function can be used to calculate the conditional probability that a sample from tissue type i, will exhibit the principal component score, x. If more than one principal component is needed to describe a sample population, then the conditional joint probability is simply the product of the conditional probabilities of each principal component (assuming that each principal component is an independent variable) for that sample population.

Fisher's Discriminant Analysis is a method that calculates a score Y for each of the samples, based on a linear combination of the variables, i.e., $$Y(N) = b_1 * X_1 * (N) + b_2 * X_2 * (N) + \ldots + b_p * X_p(N) \quad 8$$

The coefficients $b_1$ through $b_p$ are calculated so that the difference between the scores for the normals and the abnormals is maximized. Assuming that the X is normally distributed for the two groups, and assuming that the covariance s of X is the same for the two groups, then the best choice for $b_1$ is $$b1 = s^{-1} * (\text{avg. of } x_1 \text{ of norm.} - \text{avg. of } x_1 \text{ for abnorm.})$$

and similarly for $b_2$ through $b_p$. Then, a cutoff value for Y is selected and all samples with scores above the threshold are classified as belonging to the first group, normals, and samples with scores below the threshold are classified as belonging to the second group, abnormals. Since there is overlap in the distributions of Y for the two groups, some samples will be misclassified no matter where the cutoff is chosen. The cutoff is chosen to be the one that results in the lowest misclassification rate. The cutoff value given the above assumptions is $$Y_c = (n_2 Y_1 + n_1 Y_2)/(n_1 + n_2) \quad 9$$

where $n_1$ is the number of samples in group 1, and $Y_1$ is the Y score using the average values of the X variables for group 1, likewise for group 2. $Y_c$ can be adjusted from this value to reduce the FN rate at the expense of the FP rate, or vice versa, depending on the application.

Since both the b and Yc values are calculated from the data, it may be asked how well this method will classify new samples, whose values for X were not used in the above-calculations. This performance can be estimated by using cross-validation techniques. For each sample, b and Yc are calculated using the other sample data, and then the method is used to classify that sample. The misclassification error rate for all samples is measured this way is taken as an unbiased estimate of what one can expect when using Fisher's discriminate analysis to classify new samples.

The present invention uses Fisher's Discriminant Analysis to separate different categories of tissue, including diseased versus non-diseased and precancer versus non-precancer.

(v) Unbiased Evaluation of Algorithm Performance Using Cross Validation:

Cross validation is performed in instances where the sample size in relatively small, thereby providing additional confidence in the statistical relevance of the results. In this method, one sample is removed from the data set and an algorithm is developed and optimized using the remaining samples. The optimized algorithm is used to classify the removed sample. The process is repeated for each sample until all samples are classified.

III. Instrumentation

Figure 1:
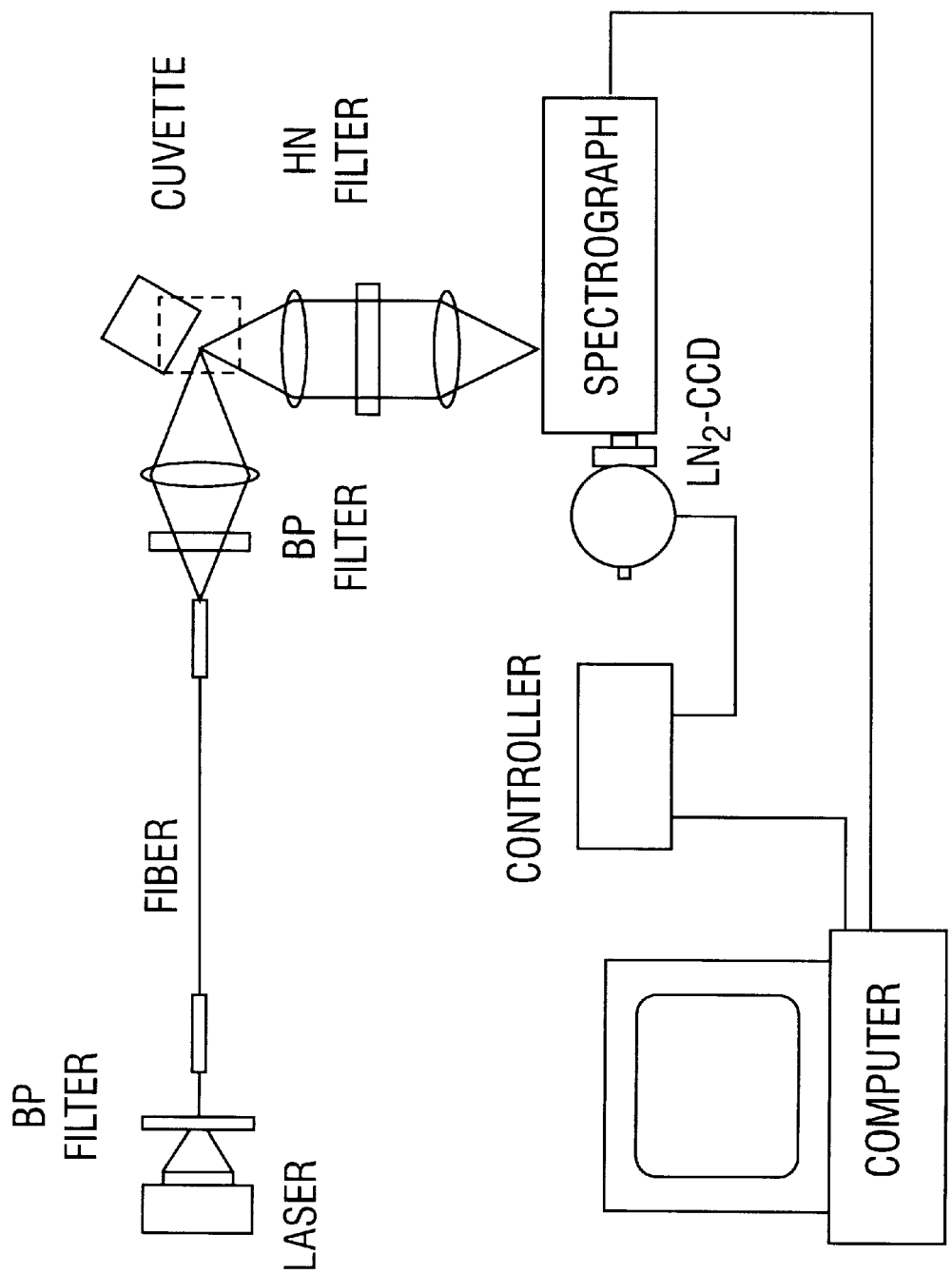
FIG. 1: Block diagram of apparatus used to measure near-infrared Raman spectra of cervical tissues in vitro in accordance with the present invention.

A Raman spectroscopy apparatus in accordance with the present invention, shown, for example, in FIG. 1, includes an illumination device for generating at least one illumination wavelength of electromagnetic radiation selected to cause a tissue sample to emit a Raman spectrum comprising a plurality of wavelengths shifted from the illumination wavelength. Typically, the light source is a laser. Also included is a Raman spectrum detector for detecting a plurality of peak intensities of the Raman spectrum at selected wavelength shifts. The system may further comprise a programmed computer connected to the Raman spectrum detector, programmed to compare each of the plurality of detected peak intensities with corresponding peak intensities of Raman spectra from normal tissue.

A 40 mW GaAlAs diode laser (Diolite 800, LiCONix, Santa Clara, Calif.) was used to excite the samples at 789 nm through a 200 micron core diameter glass optical fiber. The biopsies, measuring about 2×1×1 mm, were placed moist in a quartz cuvette with the epithelium towards the face of the cuvette and the beam. The excitation beam was incident at an angle of approximately 75° with respect to the surface normal to avoid specular reflection and was focused with a lens to a spot size of 200 µm at the tissue surface. The laser power at the sample was maintained at 25 mW (±1%). A bandpass (BP) filter with a transmission of 85% at 789 nm (±10 nm) was used to attenuate spontaneous modes and broadband DC output of the diode laser. The placement of the bandpass filter in the experimental setup was found to be significant. Spectra from the initial five pairs of tissue samples were measured with the bandpass filter placed after the laser but before the excitation fiber (FIG. 1). Because significant spectral contributions from silica were observed in this configuration, spectra from subsequent samples were measured with the filter after the excitation fiber but before the sample (FIG. 1), which dramatically reduced the silica Raman detected.

The scattered Raman signal was collected at an angle of 90 degrees from the excitation beam and imaged at the entrance slit of the detection system. A holographic notch (HN) filter (HSNF 789, Kaiser Optical Systems, Ann Arbor, Mich.) with an optical density >6 at 789 nm, was used to attenuate the elastic scattering. The detection system included an imaging spectrograph (500IS, Chromex Inc, Albuquerque, N.M.) and a liquid nitrogen cooled CCD camera (LN-1152E, Princeton Instruments, Trenton, N.J.). The spectrograph was used with a 300 gr/mm grating, blazed at 500 nm, which yielded a spectral resolution of 10 cm$^{-1}$ with an entrance slit of 100 µm.

IV. Combining Raman and Fluorescence Spectroscopy

The present invention also contemplates a method that combines NIR Raman spectroscopy, as described above, with fluorescence spectroscopy, in vitro or in vivo. This is accomplished through a light source, sequentially or simultaneously, in conjunction with an optical coupling system for the application and analysis of both kinds of data. The optical fiber is selectively coupled to ultraviolet or visible sources of electromagnetic radiation to excite fluorescence, and then selectively coupled to NIR sources to excite fluorescence-free Raman spectra. The Raman spectra may be used to improve the accuracy of the fluorescence spectra.

In one embodiment, the apparatus comprises a dichroic mirror or swing-way mirror so that each electromagnetic radiation source is selectively coupled to the optical excitation fiber. Similarly, light collected by a collection fiber may be selectively coupled to the appropriate detectors. Alternatively, a probe may house discrete sets of fluorescence and Raman excitation and detection fibers, thereby obviating the need for mirrors.

In analyzing the spectra, fluorescence may be used advantageously to identify normal tissues and low and high grade lesions. NIR Raman spectra can be used advantageously to identify inflammation and metaplasia. Alternatively, information gathered about the tissue type, in accordance with the above-described fluorescence methods, can be used to improve the Raman diagnostic capability. This is accomplished by using fluorescence spectra to calculate the posterior probability that tissue is normal, low grade or high grade SIL. Then, this classification is used as the prior probability in logistic discrimination, based on the detected Raman spectra. In yet another embodiment, information gathered with NIR Raman spectroscopy is used to calculate the posterior probability that the tissue is inflamed or metaplastic. Then, this information is used as the prior probability in logistic discrimination, based on the detected fluorescence spectrum. By the same token, Raman can improve the diagnostic performance of fluorescence by reducing misclassification of inflammation and metaplasia as precancer.

In one embodiment, a sample is illuminated with electromagnetic radiation wavelengths of about 317–357 nm, about 360–400 nm and about 440–480 nm to produce three fluorescence intensity spectra. From the spectra, there are detected a plurality of emission frequencies from said fluorescence intensity spectra. A probability that the sample is abnormal is then established from the emission frequencies. Advantageously, the data are preprocessed and then subjected to a statistical analysis to yield a set of principal components that provide a statistical determination of significant differences between normal tissues and various forms of abnormal tissue, including low grade SIL and high grade SIL.

In a more specific embodiment, the illumination wavelengths are 337, 380 and 460, and the emission frequencies are about 410 nm, about 460 rum, about 510 nm and about 580 nm for an illumination of about 337 nm; about 460 nm, about 510 nm, about 580 nm, about 600 nm and about 640 nm for an illumination of about 380 nm; and about 510 nm, about 580 nm, about 600 nm, about 620 nm, about 640 nm and about 660 nm for an illumination of about 460 nm.

V. Examples

The following examples are included to demonstrate preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1: METHODS

The protocol for this study was reviewed and approved by the Internal Review Board at the University of Texas at Austin and the Surveillance Committee at the University of Texas MD Anderson Cancer Center. Twenty colposcopy patients referred to the University of Texas MD Anderson Cancer Center on the basis of abnormal cervical cytology participated in this study. Informed consent was obtained from each patient. One colposcopically normal and one colposcopically abnormal site were biopsied from each patient. Biopsies were snap frozen in liquid nitrogen and stored at -85° C. until Raman spectra were measured. Following spectroscopic measurements, biopsies were fixed in 10% buffered formalin and sent for histopathologic evaluation. Consensus diagnosis of all pathologic processes present in the samples was provided by two board certified clinical pathologists.

Samples were classified using the Bethesda system, a cytological classification scheme that has been recently extended to the classification of cervical biopsies (Table 1). Precancerous lesions, called squamous intraepithelial lesions (SILs), include human papilloma viral infection (HPV—an oncogenic virus), mild, moderate and severe precancers. SILs are further divided into low grade SILs (HPV, mild precancers) and high grade SILs (moderate and severe precancers). Clinically, this distinction is important as low grade SILs are typically followed but not treated and high grade SILs are usually treated. An individual biopsy could contain more than a single pathology; however, spectroscopic results were correlated to the most severe pathologic diagnosis of the biopsy.

TABLE I

The Bethesda classification scheme extended for cervical biopsies.

| | Bethesda Classification Scheme | | |
|---|---|---|---|
| | | Squamous Intraepithelial Lesion (SIL) | |
| | Non-SIL | Low Grade SIL | High Grade SIL |
| Histo-Pathologic Diagnoses | Normal Inflammation Metaplasia | HPV Mild Precancer | Moderate Precancer Severe Precancer |

NIR Raman spectra were measured in vitro using the system shown in FIG. 1. Raman spectra were measured from 500–2000 cm$^{-1}$ relative to the excitation frequency and each sample spectrum was integrated for 15 minutes.

Each background subtracted spectrum was corrected for wavelength dependent response of the spectrograph, camera, grating and filters. The system was calibrated daily for wavenumber and throughput variations using naphthalene, rhodamine 6G and carbon tetrachloride. The Raman shift was found to be accurate to ±7 cm$^{-1}$ and the calibrated intensity was accurate to ±12% of the mean. To verify that accurate spectra could be obtained from highly fluorescent samples, rhodamine 6G powder was used as a standard, since it has well documented fluorescence and Raman characteristics. Since the Raman intensity of this standard is substantially greater than that of tissue, a weak standard was also created to verify that accurate spectra could also be obtained from highly elastic samples with high fluorescence quantum yields and low Raman cross-sections. This weak solid standard (KIR) consists of potassium iodide (which is highly scattering but emits little or no Raman signal) and rhodamine 6G (which is highly fluorescent and is also an intense Raman scatterer) in a proportion of 10,000:1 in weight. This mixture was created such that its Raman intensity is similar to that from tissue for the same integration times.

Data Preprocessing:

Tissue spectra obtained using the system in FIG. 1 contain a combination of Raman scattering, intrinsic tissue fluorescence and noise. Significant data preprocessing is required to yield the tissue vibrational spectrum. Several techniques to reduce the noise and fluorescence distortion were attempted and tested on spectra of two rhodamine standards. The observed noise was established to be approximately gaussian (M. A. Schulze, *Doctoral Dissertation*, University of Texas at Austin (1994), which is hereby incorporated by reference. This implies that simple filtering techniques would be effective in smoothing the curves. Optimal results were obtained when the spectrum was convolved with a gaussian whose full width half maximum was equal to the resolution of the system (G. W. Small, M. A. Arnold, L. A. Marquardt, Anal Chem, 65, 3279 (1993), which is hereby incorported by reference. This technique discards any signal with bandwidth less than the resolution of the system. The filtered signal still contains both fluorescence and Raman signals. A simple and accurate method to subtract fluorescence is to fit the spectrum containing both Raman and fluorescence information to a polynomial of high enough order to describe the fluorescence lineshape but not the higher frequency Raman lineshape (R. Manoharan, *Personal Communication*, (1994), which is hereby incorporated by reference. A 5th degree polynomial was found to work in this study. The best fit polynomial was then subtracted from the spectrum to yield the Raman signal alone. Rhodamine and KIR spectra were used to validate the signal processing techniques and verify that the technique did not distort the resultant spectrum. Each tissue spectrum was similarly preprocessed.

EXAMPLE 2: STATISTICAL METHODS

Analysis Methods:

Both empirical and multivariate techniques were used to explore the diagnostic capability of NIR Raman spectra of cervical tissues. Peak intensities were measured from each processed tissue spectrum; intensities and ratio of intensities were compared for SILs and non-SILs. Multivariate statistical algorithms were developed for tissue differentiation following a procedure originally described to develop fluorescence based algorithms. The method includes five steps: (i) data processing, (ii) dimension reduction using Principal Component Analysis (PCA), (iii) selection of diagnostically important principal components using the unpaired Student's t-test, (iv) development of a classification algorithm using Fisher Discriminant Analysis (FDA), (v) and unbiased evaluation of algorithm performance using cross validation.

Each smoothed, fluorescence subtracted spectrum contained 727 variables (intensities at each Raman shift). To reduce the degree of oversampling, a moving average was taken and the spectrum was reduced to 364 variables. Spectra from all samples were thus processed and combined to form a data matrix where each row contained a sample processed spectrum and each column contained the intensity of the Raman scattering at a particular frequency. Principal Component Analysis (PCA) was used to describe the original Raman spectra (intensity at each Raman shift) as a sum of a small orthogonal set of linear combinations of the original variables called principal components that account for 99% of the variance in the original data. Each principal component can then be easily related to the original variables using component loadings which represent the correlation between the principal component and the original variables. The hypothesis that the means of the principal component scores of two tissue categories, SILs and non-SILs, are different was tested for each principal component. A standard two-sided unpaired t-test (J. L. Devore, *Probability and Statistics for Engineering and Science*, (Brooks/Cole, Pacific Grove, Calif., 1992), which is hereby incorporated by reference, was performed to determine diagnostically significant principal components. Principal components that were statistically significant under the hypothesis were retained for further analysis.

Fisher's Discriminant Analysis (FDA) was used as a classification technique to discriminate SILs and non-SILs. FDA is a statistical technique that uses linear combinations of independent variables to discriminate between two groups such that the misclassification rates are minimized (A. Albert, E. K. Harris, *Multivariate Interpretation of Clinical Laboratory Data*, (Marcel Dekker, New York, 1987), which is hereby incorporated by reference. FDA yields optimal results for normally distributed data when the prior probability which accounts for the differences in sample size of the two groups and the cost of misclassifying a sample in a particular group are included. The prior probability was determined by calculating the percentage of each diagnostic group in the data set. The cost of misclassification of a particular group can be varied between 0 and 1 with the criterion that the sum of the costs for each diagnostic group equals one. The cost was optimized to minimize the number of samples misclassified. Component loadings were used to select those frequencies that were most highly correlated to the significant principal components (with a cut-off correlation coefficient of 0.6). PCA was then repeated on the new reduced data matrix whose rows correspond to the individual samples and columns correspond to the intensities at the selected frequencies.

Given the small number of samples, cross validation was used to estimate the algorithm performance in an unbiased manner. In this method, one sample spectrum was removed from the data set and the entire algorithm (as described above) was developed and optimized using the remaining samples. The optimized algorithm was then used to classify the held out sample. This process was repeated for each sample until all the samples were classified.

The performance of algorithms was quantified in terms of sensitivity and specificity of diagnosis. Table 2 defines these terms as it pertains to medical diagnosis. The gold standard for any diagnostic technique is that provided by histo-pathologic diagnosis with 100% sensitivity and specificity or 0% false positives and false negatives error rates.

TABLE II

Definition of terms used to evaluate algorithm performance for medical diagnosis.

| Spectroscopy Diagnosis | Histo-Pathologic Diagnosis | |
|---|---|---|
| | Non-SIL | SIL |
| Non-SIL | True Negatives (TN) | False Negatives (FN) |
| SIL | False Positives (FP) | True Positives (TP) |
| Number of samples | N = TN + FP Specificity = TN/N | D = FN + TP Sensitivity = TP/D |

Spectra were measured from chromophores that could potentially contribute to tissue Raman scattering. The chromophores selected were based on a review of the literature as well as the biochemistry and histology of cervical tissue. They were collagen, elastin, reduced nicotinamide adenine dinucleotide (NADH), flavin adenine dinucleotide (FAD), glucose, glycogen, glucose 1-phosphate, hemoglobin, nucleic acids, tryptophan, tyrosine and various phospholipids. These chromophores were obtained commercially (Sigma Inc, St. Louis, Mo.) and spectra were measured in their pure powdered form, contained in a quartz cuvette. Integration times of the chromophores spectra varied from 5 to 15 minutes to obtain spectral intensities of the same order as tissue. Chromophore spectra were processed using the same methods as tissue spectra. Chromophore and tissue Raman spectra were qualitatively compared to tentatively identify the origin of the observed tissue peaks. A quantitative understanding was also attempted; tissue spectra were fit to a linear combination of chromophore spectra. Relative contributions of each chromophore was varied in an iterative procedure to minimize the sum of the squares of the difference in the intensity of the measured tissue and fitted chromophore spectra between 600 and 1800 $cm^{-1}$.

EXAMPLE 3: RESULTS

FIG. 2 shows spectra of pure rhodamine and the weak KIR standard (without the spectral component of KI), measured with the bandpass filter either before or after the excitation fiber. Spectra of pure rhodamine were similar in either case and agreed well with published spectra. However, the spectra of the weak KIR standard with intensity similar to tissue, depended on the position of the bandpass filter. When the bandpass filter was placed before the excitation fiber, significant peaks at 626 and 818 $cm^{-1}$ and an additional smaller peak at 1078 $cm^{-1}$ were observed (FIG. 2C). These spectral features are attributed to the Raman signal from silica produced in the excitation fiber (A. Mahadevan-Jansen, R. Richards-Kortum, Jour of Biomedical Optics, 1, 40 (1996); 30 M. L. Myrick, S. M. Angel, R. Desideric, Applied Optics, 29, 1333 (1990); 31. C. D. Newman, G. G. Bret, R. L. McCreery, Applied Spectroscopy, 46, 262 (1992), all of which are hereby incorporated by reference. When the bandpass filter is placed before the excitation fiber, silica Raman from the fiber is incident on the sample and can be differentially reflected back into the collection optics and hence the detector. This effect of silica Raman is highlighted in highly scattering samples such as tissue but is not apparent in spectra from intense Raman scatterers such as rhodamine and naphthalene. However, when the bandpass filter was placed after the excitation fiber, the KIR spectrum (without the spectral component of KI) was similar to the rhodamine spectrum (FIG. 2A and 2B). Placing the bandpass filter after the excitation fiber blocks most of the silica Raman lines from the samples and hence the detector. Although some contribution of silica can be seen around 626 and 818 $cm^{-1}$, this effect is a small one and does not interfere with the detection of the rhodamine peaks.

Two of the twenty sample pairs studied were discarded due to experimental errors. Of the remaining 18 sample pairs, histologically, there were 19 normal, 2 metaplasia, 4 inflammation, 2 HPV and 9 precancers. One HPV and two precancer samples had focal lesions. Clinically, two types of differentiation are important: (i) SILs from non-SILs and (ii) high grade SILs from low grade SILs. In this study, the sensitivity and specificity of colposcopy for differentiating SILs and non-SILs were 100% and 73% when compared to histology. Colposcopy was not utilized to differentiate between high grade and low grade SILs. Raman algorithms were developed to achieve both types of differentiation. All samples were analyzed together regardless of the experimental setup used for measurement.

Figure 3A:
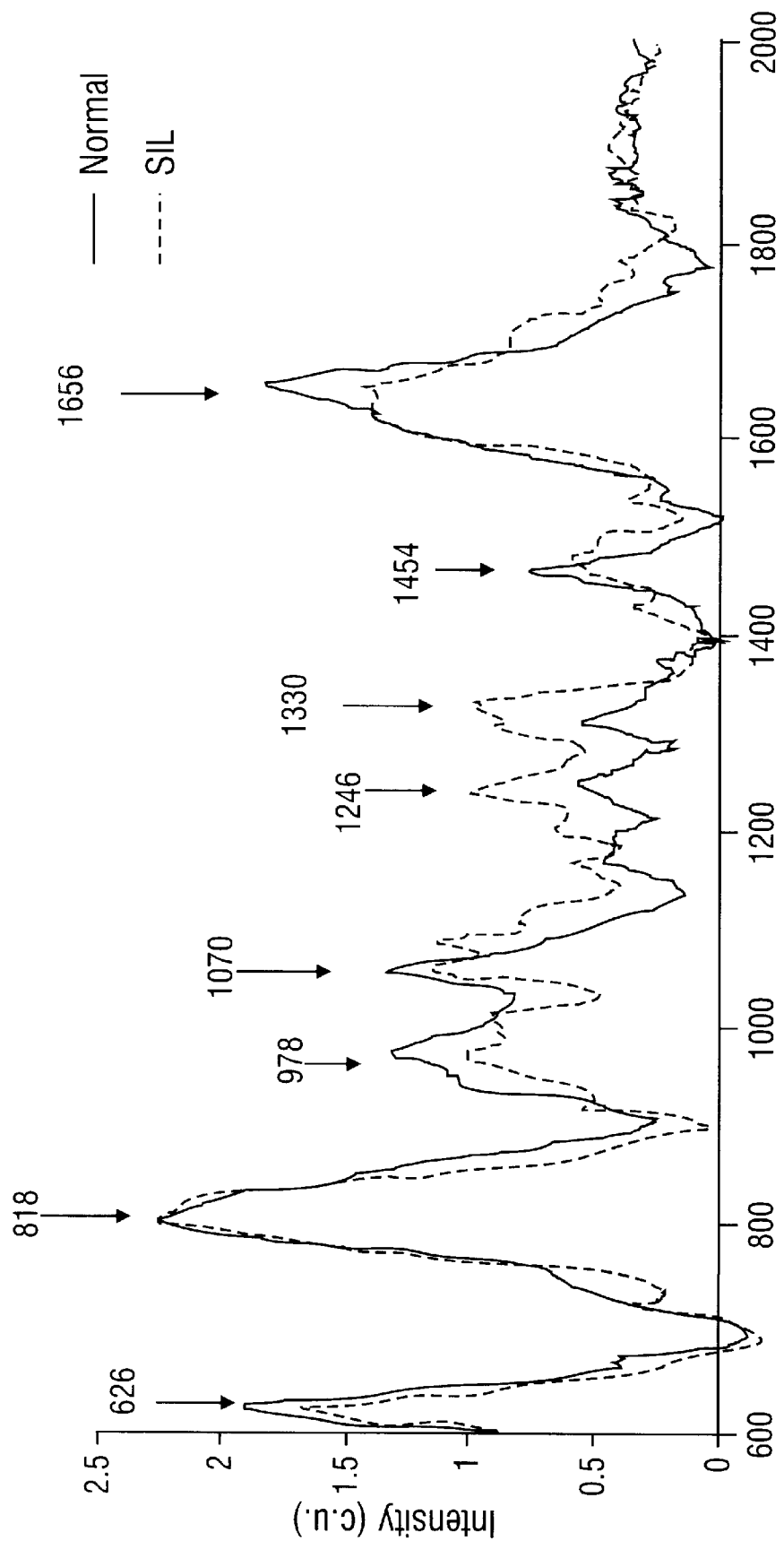
FIGS. 3A and 3B: Tissue Raman spectra for a pair of normal and SIL samples from two different patients where (FIG. 3A) the bandpass filter is placed before the excitation fiber and (FIG. 3B) the bandpass filter is placed after the excitation fiber.
Figure 3B:
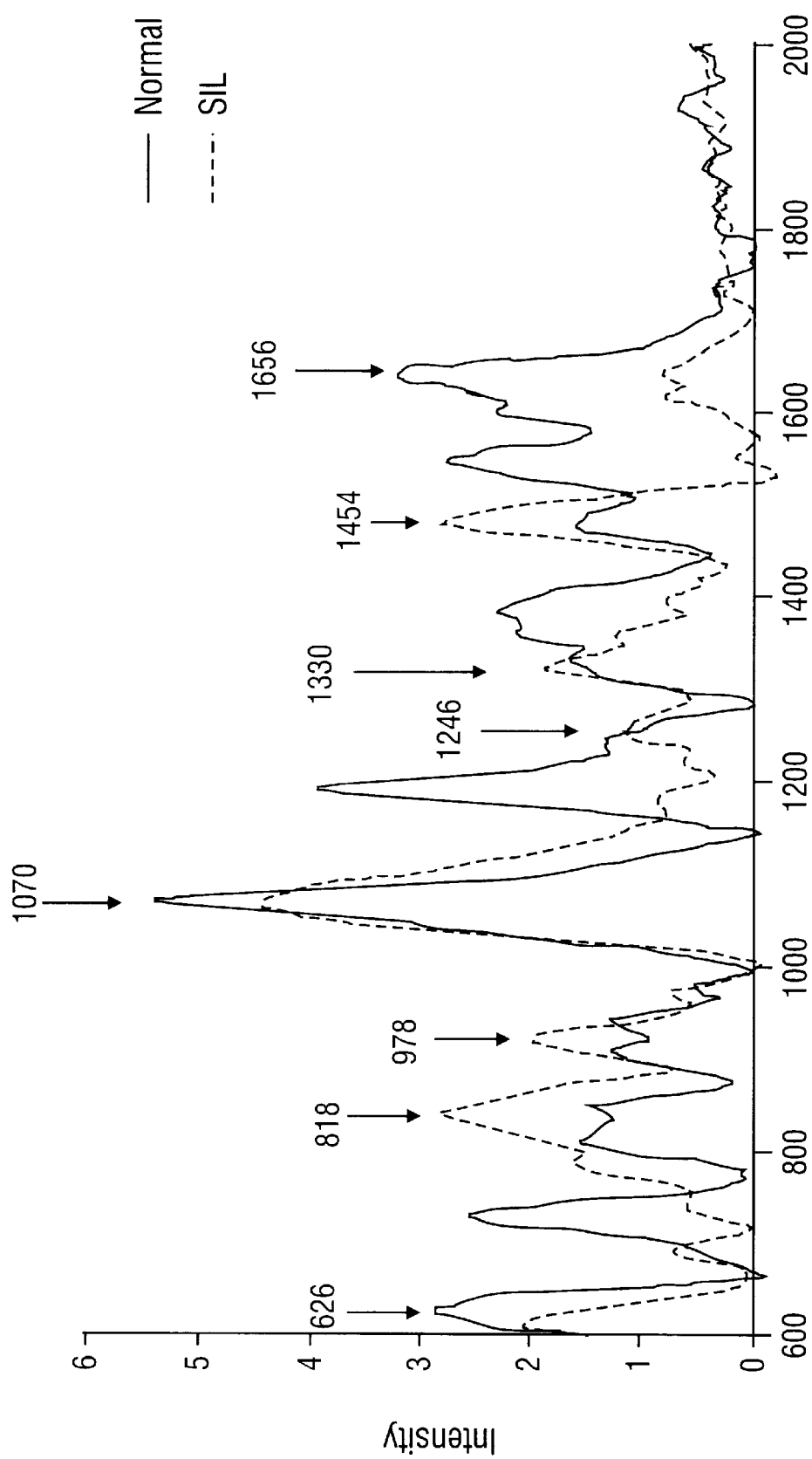

FIG. 3 shows two typical pairs of tissue Raman spectra, one measured with the bandpass filter placed before the excitation fiber (FIG. 3A) and the other measured with the filter after the excitation fiber (FIG. 3B). FIG. 3A shows intense peaks at 626 and 818 $cm^{-1}$ primarily due to silica as was observed in FIG. 2C. This spectrum was typical of tissue spectra obtained with the bandpass filter before the excitation fiber. The silica contribution was significantly reduced in the remaining samples where the filter was placed before the excitation fiber as is observed in FIG. 3B. Several spectral features previously hidden by the intense peaks at 626 and 818 $cm^{-1}$ are now visible. Spectral regions above 900 $cm^{-1}$ are similar in FIGS. 3A and 3B.

Primary tissue Raman peaks are observed at 626, 818, 978, 1070, 1246, 1330, 1454, and 1656 $cm^{-1}$ (±10 $cm^{-1}$). Other peaks include those at 690, 760, 850, 870, 1006, 1150, 1175, 1198, 1400, 1576 $cm^{-1}$, not observed consistently in all samples. The intensity of the various Raman bands show a significant patient to patient variability. In an attempt to account for this inter-patient variability, each peak in a spectrum was normalized to the corresponding peak of the colposcopically normal sample from the same patient. Thus all colposcopically normal samples have a peak intensity of one. Both normalized and unnormalized spectra were analyzed for diagnostic information.

Figure 4A:
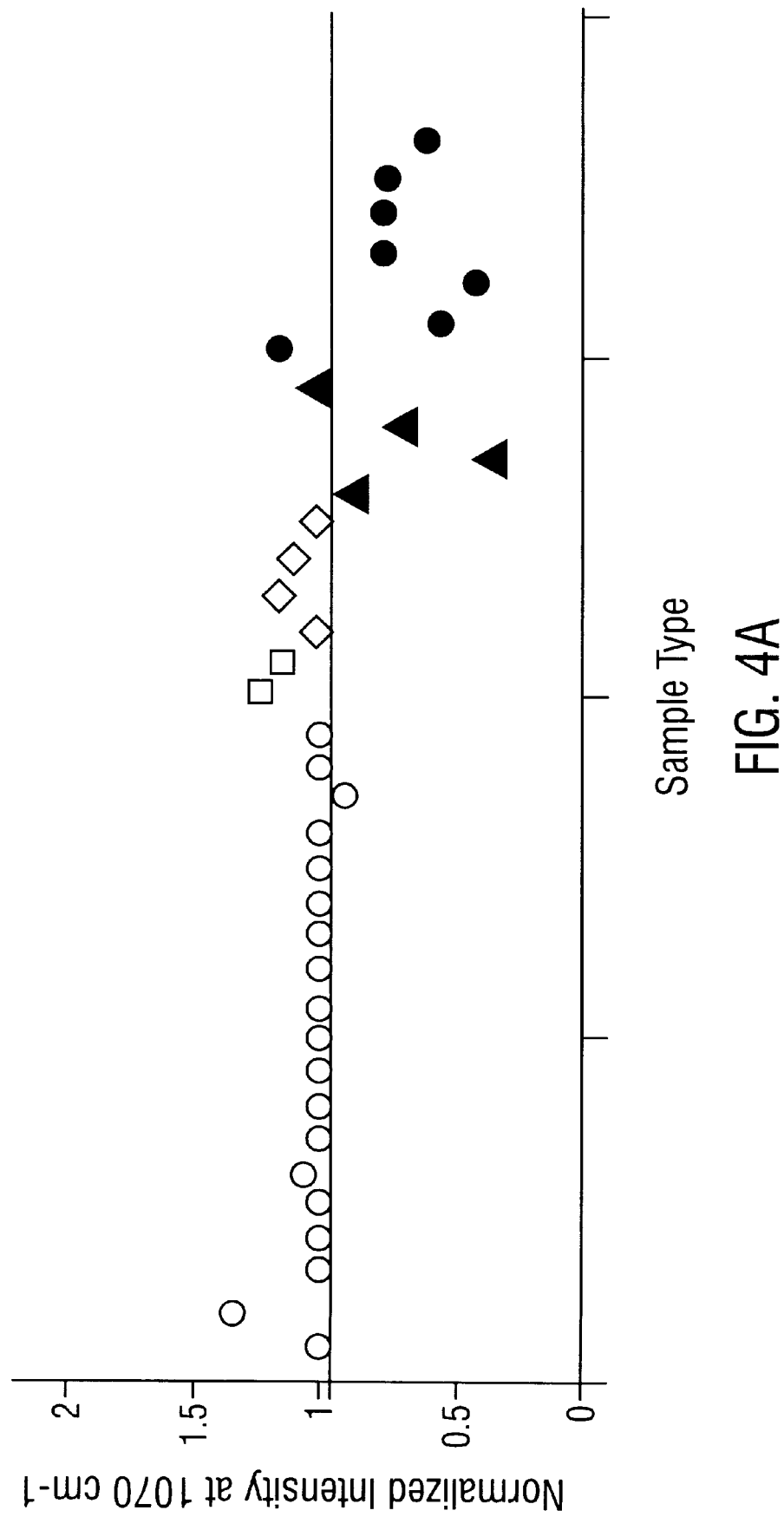
FIGS. 4A and 4B.
Figure 4B:
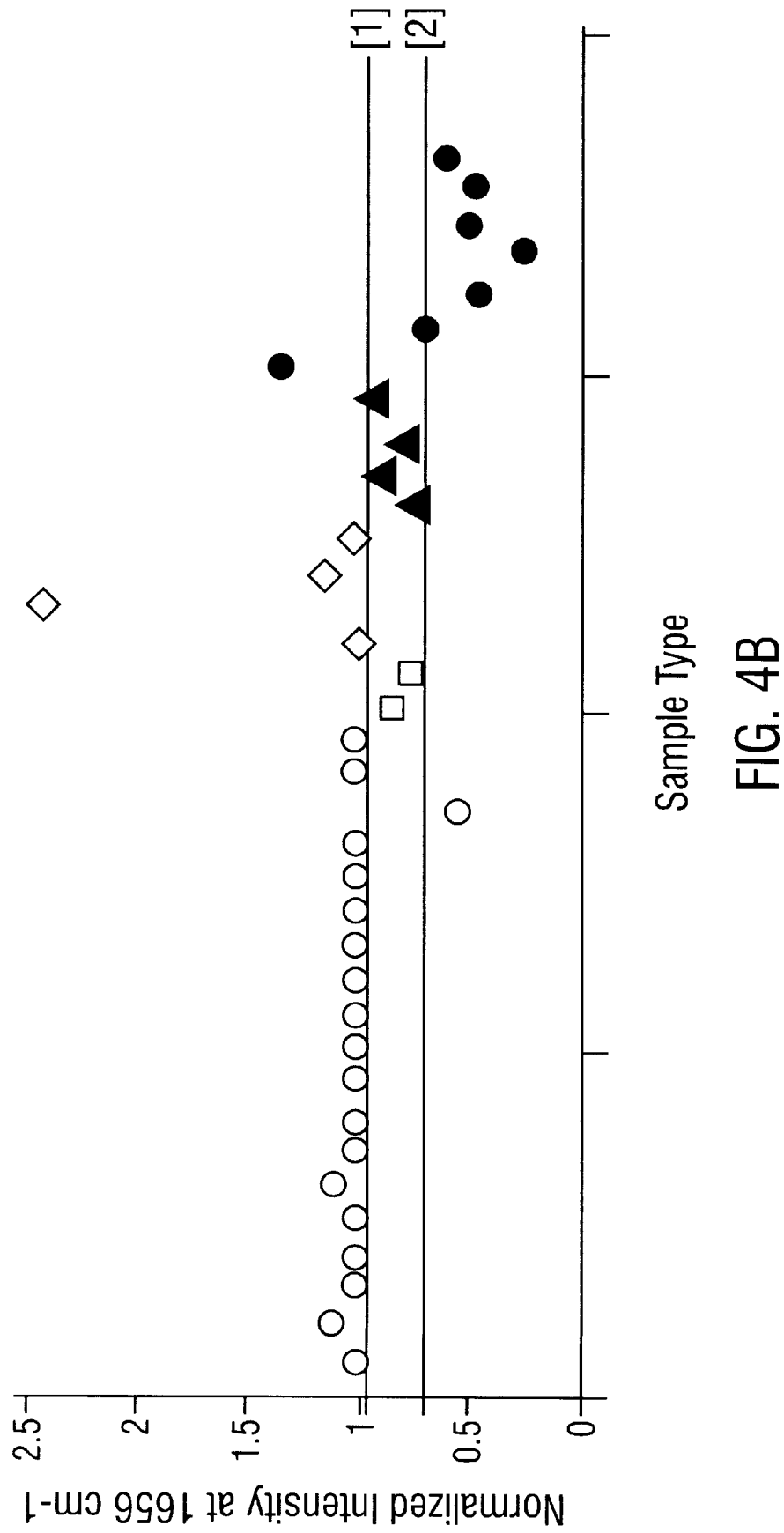

Each of the peaks observed contains some diagnostic information and can differentiate between tissue categories with varying accuracy. Using paired analysis, the bands at 1070 and 1656 cm$^{-1}$ can each differentiate SILs from non-SILs. At both bands, the intensity of the non-SIL is generally greater than the intensity of the SIL. This is illustrated in FIGS. 4A and 4B. The intensity at 1070 cm$^{-1}$ correctly classifies all metaplasia and inflammation samples as non-SILs (FIG. 4B). Of the 2 SILs incorrectly classified at 1070 cm$^{-1}$, one has focal precancer and the other is a sample with focal HPV. Only one normal sample is misclassified as SIL. A sensitivity and specificity of 82% and 96% are achieved. FIG. 4B indicates the diagnostic capability of the band at 1656 cm$^{-1}$. The normalized peak intensity at 1656 cm$^{-1}$ can differentiate SILs from non-SILs using decision line (1) with a sensitivity and specificity of 91% and 88%. The focal precancerous sample incorrectly classified at 1070 cm$^{-1}$ is again misclassified. Metaplastic samples are misclassified as SILs. This peak can also differentiate between high grade and low grade SILs. Using decision line (2), this peak can separate high grade and low grade SILs with a sensitivity and specificity of 86% and 100%. Metaplasia samples, misclassified as SILs, are separated from the high grade samples and only one normal sample is misclassified as a high grade SIL. This peak separates high grade SILs from all others tissues (non-SILs and low grade SILs) with a sensitivity and specificity of 86% and 98%.

Figure 5A:
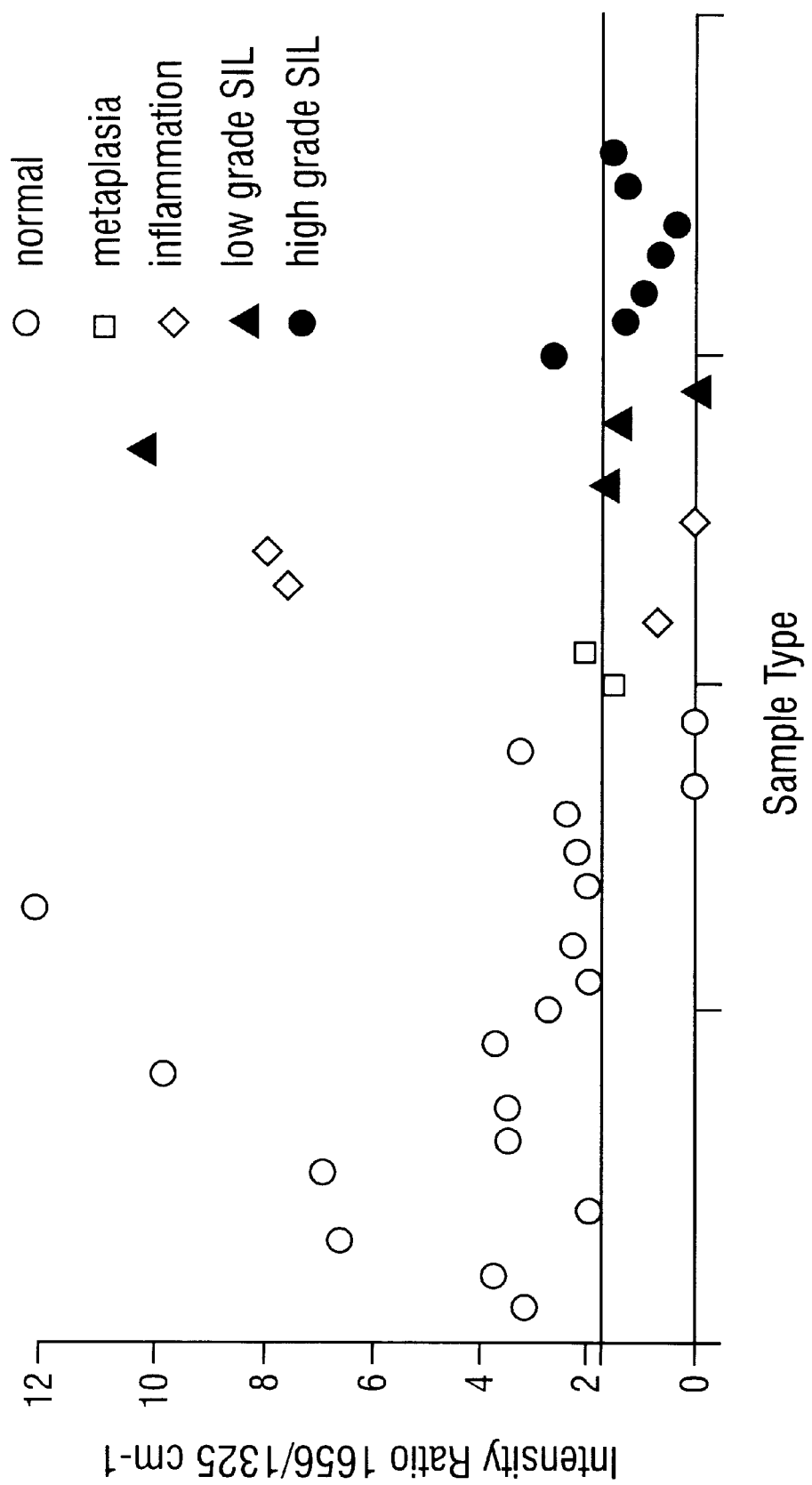
FIGS. 5A and 5B.
Figure 5B:
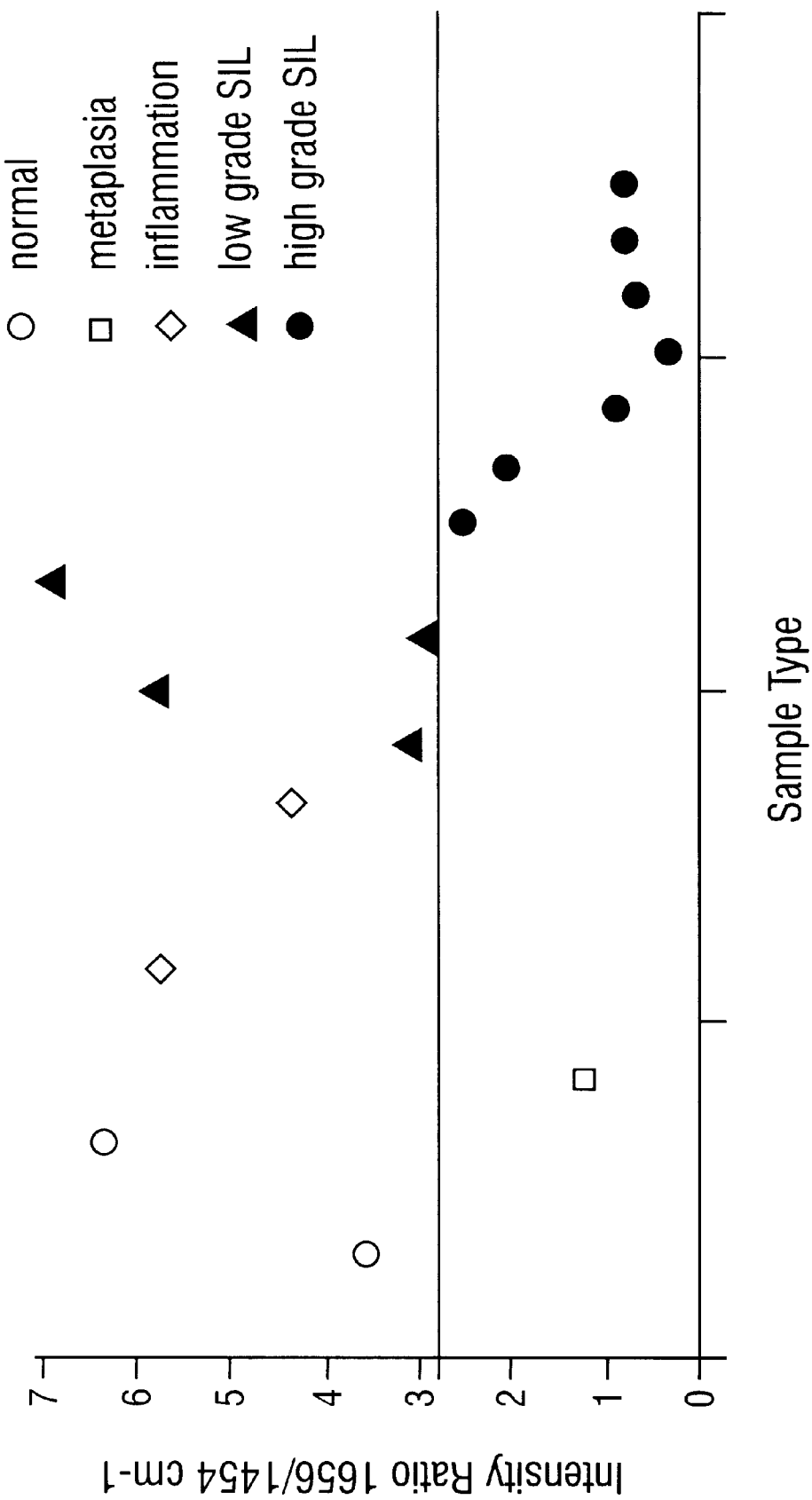

Using intensities in a paired manner to account for inter-patient variability requires prior measurement from a known normal sample. Differentiation can also be achieved without prior measurement from a known normal sample using the peaks at 1330, 1454 and 1656 cm$^{-1}$ with comparable performance for precancer detection. The ratio of unnormalized peak intensities at 1656 and 1330 cm$^{-1}$ can differentiate SILs from non-SILs with a sensitivity and specificity of 82% and 80% respectively (FIG. 5A). The two SIL samples incorrectly classified are focal lesions and are the same samples misclassified at 1070 cm$^{-1}$. Half of the samples with inflammation and metaplasia are also misclassified as SILs, resulting in a poorer specificity compared to the paired algorithms. As a second step, the ratio of unnormalized intensities at 1656 and 1454 cm$^{-1}$ can differentiate high grade SILs from low grade SILs with a sensitivity and specificity of 100%. Non-precancerous samples that were misclassified as SILs in FIG. 5A were also analyzed using this algorithm. All except one of the previously misclassified non-SILs are separated from the high grade SILs using the algorithm from FIG. 5B. The ratio of intensities at 1656 to 1454 cm$^{-1}$ was also used by Liu et al and was shown to separate malignant and non-malignant cervical tissues.

Multivariate statistical techniques were used to develop and evaluate algorithms that differentiate SILs and non-SILs using the tissue Raman spectra. Due to the small number of low grade SIL samples, multivariate analysis was not used to develop an algorithm to discriminate high grade and low grade SILs.

PCA was employed on the data matrix consisting of the processed tissue Raman spectra of all samples. Twenty-six principal components were required to describe 99% of the original variance in the data; thus significant data reduction was achieved. Six principal components—PC2, PC3, PC6, PC10, PC11 and PC22, accounting for 15%, 9%, 5%, 2%, 2% and 0.5% of the variance respectively, showed statistically significant differences (p<0.1) between SILs and non-SILs. Table 3 gives the means, standard deviations and p-values of the six statistically significant principal component scores.

TABLE III

The means, standard deviations, variance and p-values of the six statistically significant principal components calculated for the data matrix consisting of the processed Raman spectra.

|  | Mean ± std dev (SIL) | Mean ± std dev (non-SIL) | Variance | p-value | Fisher Coefficient |
| --- | --- | --- | --- | --- | --- |
| PC2 | −1.69 ± 2.06 | 2.79 ± 3.4 | 15% | 0.032 | 0.3 |
| PC3 | 2.53 ± 3.44 | 5.08 ± 3.96 | 9% | 0.018 | 0.29 |
| PC6 | −5.38 ± 1.76 | −6.3 ± 3.35 | 5% | 0.068 | −0.18 |
| PC10 | −1.81 ± 1.6 | −2.98 ± 1.97 | 2% | 0.079 | −0.56 |
| PC11 | 1.46 ± 1.5 | 0.73 ± 1.8 | 2% | 0.078 | −0.42 |
| PC22 | 1.44 ± 0.8 | 1.85 ± 0.86 | 0.5% | 0.071 | 0.98 |

Figure 6:
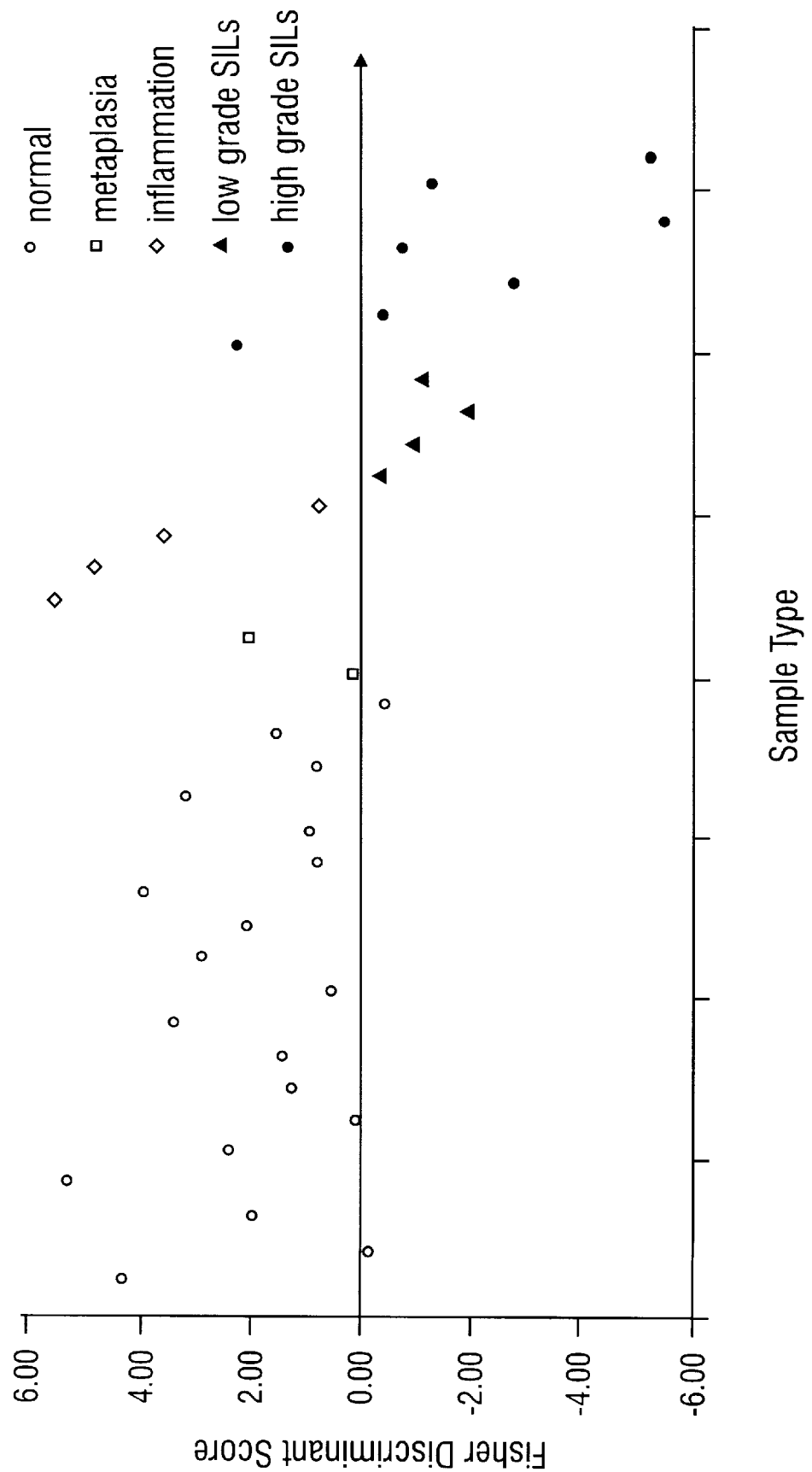
FIG. 6: Fisher Discriminant scores of all samples using statistically significant principal components calculated for the processed Raman spectra. The decision line separates SILs and non-SILs with a sensitivity and specificity of 91% and 90%.

FDA was used to develop an optimized classification algorithm which separates non-SILs and SILs. The algorithm was developed and evaluated using principal component scores of all 36 samples. The corresponding Fisher coefficients of the optimal algorithm are also shown in Table 3. FIG. 6 shows the Fisher discriminant score for each sample. Despite the overlap in the distributions of the principal component scores used for diagnosis, the algorithm can differentiate SILs and non-SILs with a sensitivity and specificity of 91% and 90%. One SIL sample with a focal lesion and two normal samples are misclassified. The performance of this algorithm is comparable to the performance of the algorithm based on empirically selected intensities.

Figure 7C:
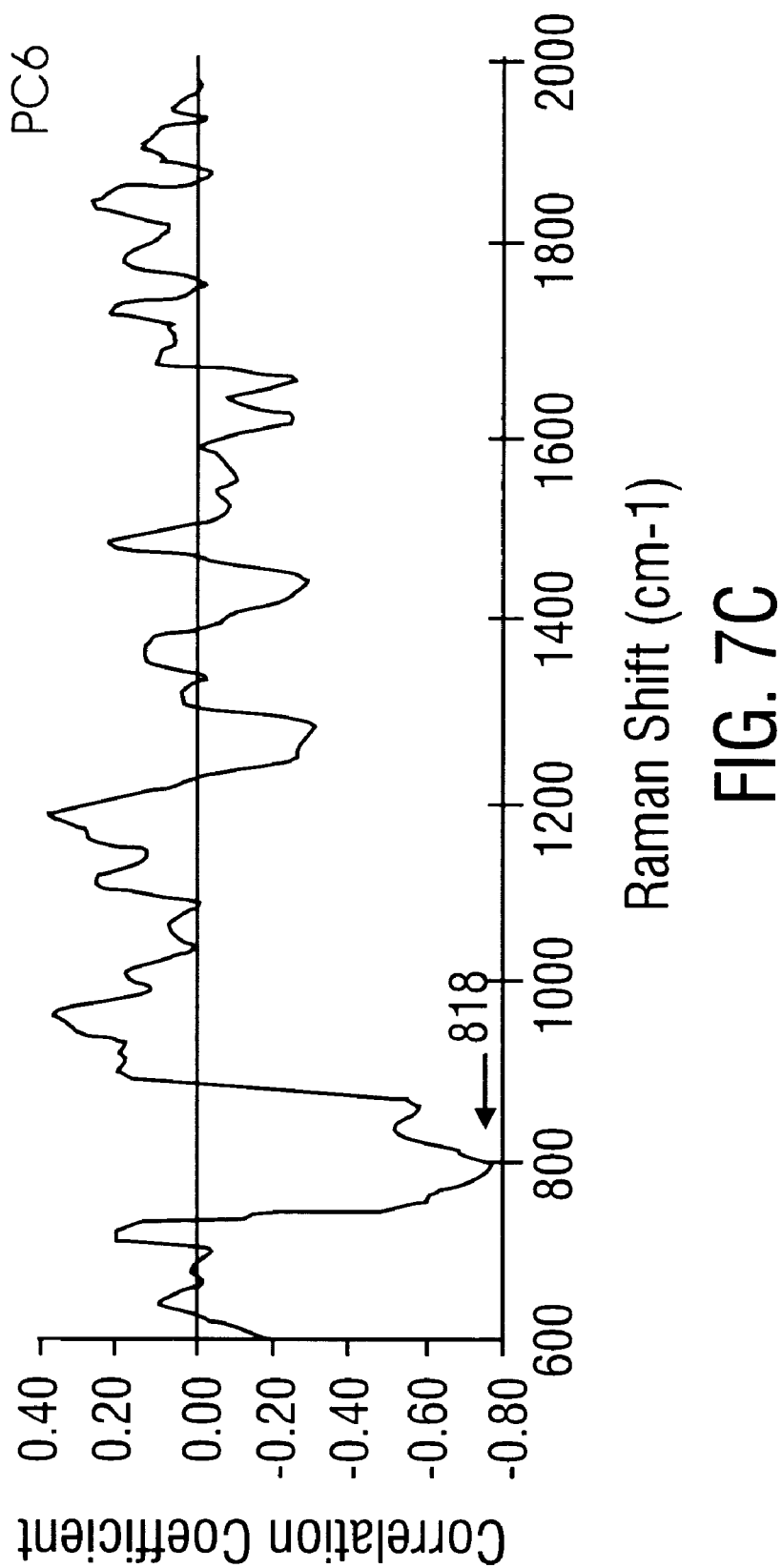
FIG. 7: Component loadings corresponding to three of the six statistically significant principal components (PC2, PC3, PC6) calculated for the entire Raman spectrum. The eight highly correlated Raman bands selected for further analysis are indicated.

The component loadings, which represent the correlation between each principal component and the original processed Raman spectra, were used to identify those frequencies which contribute most to the diagnostic ability. Only component loadings associated with PC2, PC3 and PC6 showed correlation coefficients greater than 0.6. These are the principal components which showed the most statistically significant differences between SILs and non-SILs. FIG. 7 illustrates the three component loadings and indicates the seven peak locations with coefficients greater than 0.6 that were retained for further analysis. Component loading 2 is highly and negatively correlated at 1246, 1330, and 1454 cm$^{-1}$. Evaluation of spectra at these bands indicates an increase in intensity in SILs as compared to non-SILs. Component loading 3 is highly and positively correlated at 626, 1070 and 1656 cm$^{-1}$. The intensity of the SILs at these bands is lower than the non-SILs. Component loading 6 is highly and negatively correlated at 818 cm$^{-1}$. The seven selected frequencies correspond to all except one of the primary peaks (at 978 cm$^{-1}$) observed in the typical Raman spectra. New, reduced data matrices were constructed with columns corresponding to the 8 frequencies identified from the original spectra and from the component loadings. Rows corresponded to individual samples. The procedure of algorithm development was repeated with these reduced matrices. Best results were obtained using 8 intensities; seven at frequencies selected from the component loadings plus that at 978 cm$^{-1}$.

Figure 8:
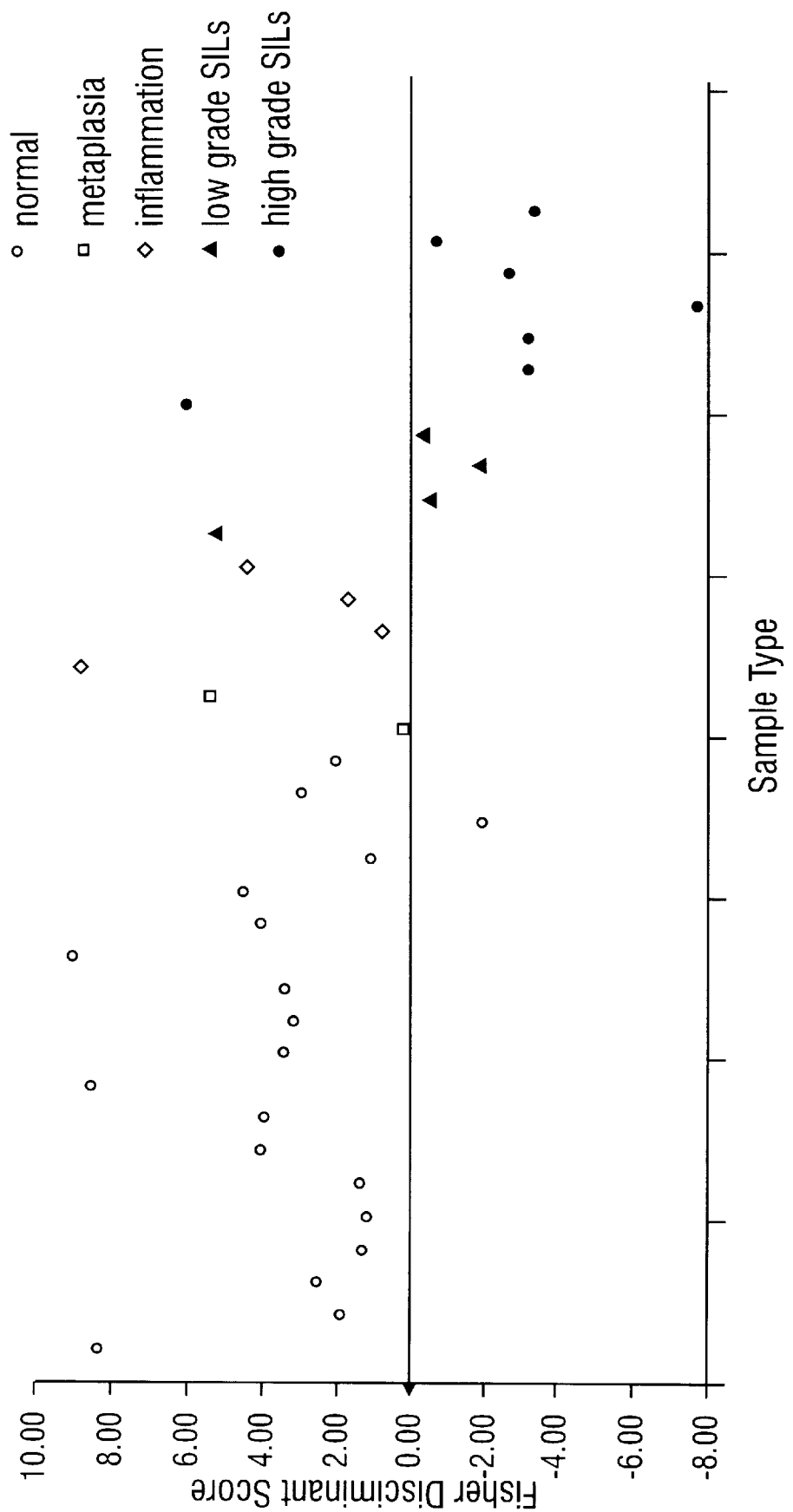
FIG. 8: Fisher Discriminant scores calculated using cross validation from statistically significant principal component scores for the reduced data matrix containing 8 spectral Raman bands. The decision line separates SILs and non-SILs with a sensitivity and specificity of 82% and 96%.

Eight principal components accounted for 99% of the variance in the reduced spectra, indicating that further spectral data reduction is not possible. In the reduced data set, PC1 and PC2 which account for 45% and 12% of the variance respectively, showed statistically significant differences between SILs and non-SIL,s (Table 4). FIG. 8 shows the Fisher discriminant score for each sample obtained using cross validation. When compared to histology, the algorithm gives an unbiased estimate of the sensitivity and specificity as 82% and 96% respectively. These are similar to results achieved with multivariate analysis of the entire spectrum. Two SIL samples with focal lesions misclassified in the algorithm of FIG. 4A were again classified as non-SIL.

TABLE IV

The means, standard deviations, variance and p-values of the two statistically significant principal components calculated for the reduced data matrix consisting of intensities at 8 frequencies.

|  | Mean ± std dev (SIL) | Mean ± std dev (non-SIL) | Variance | p-value |
|---|---|---|---|---|
| PC1 | 3.31 ± 1.38 | 4.32 ± 2.18 | 45% | 0.03 |
| PC2 | −1.03 ± 0.97 | −2.36 ± 0.88 | 12% | 0.0004 |

Figure 9A:
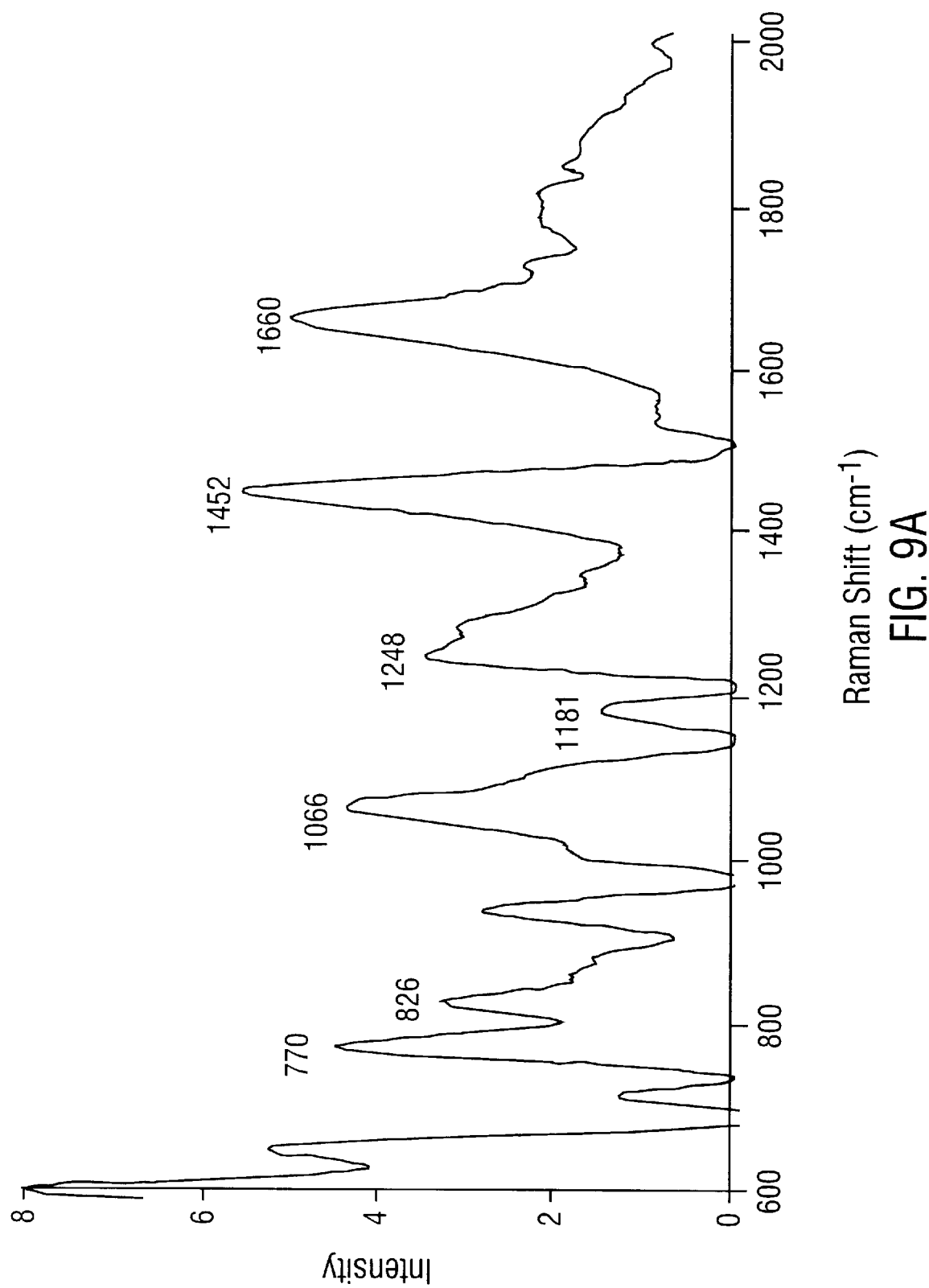
Figure 9B:
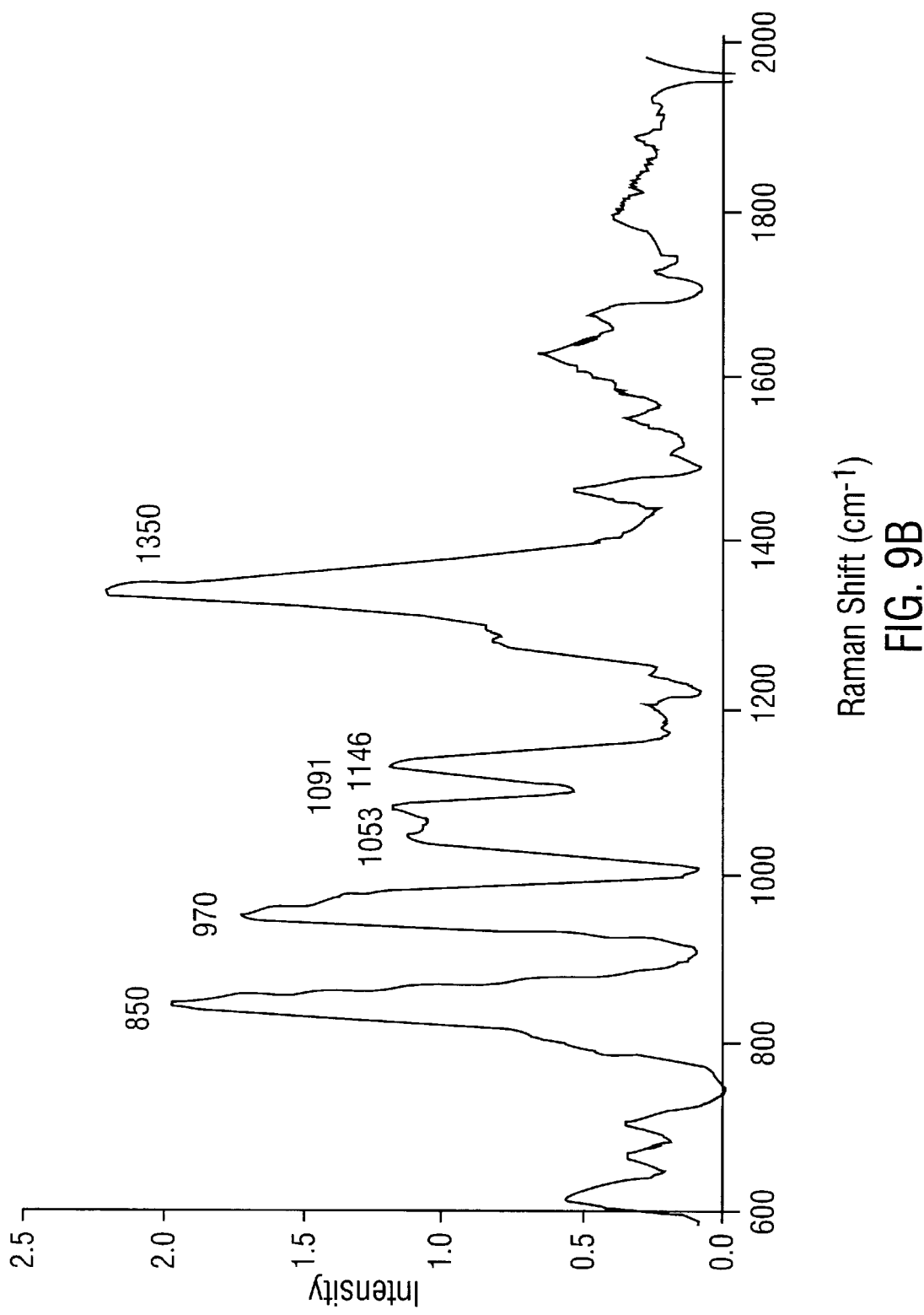
Figure 9D:
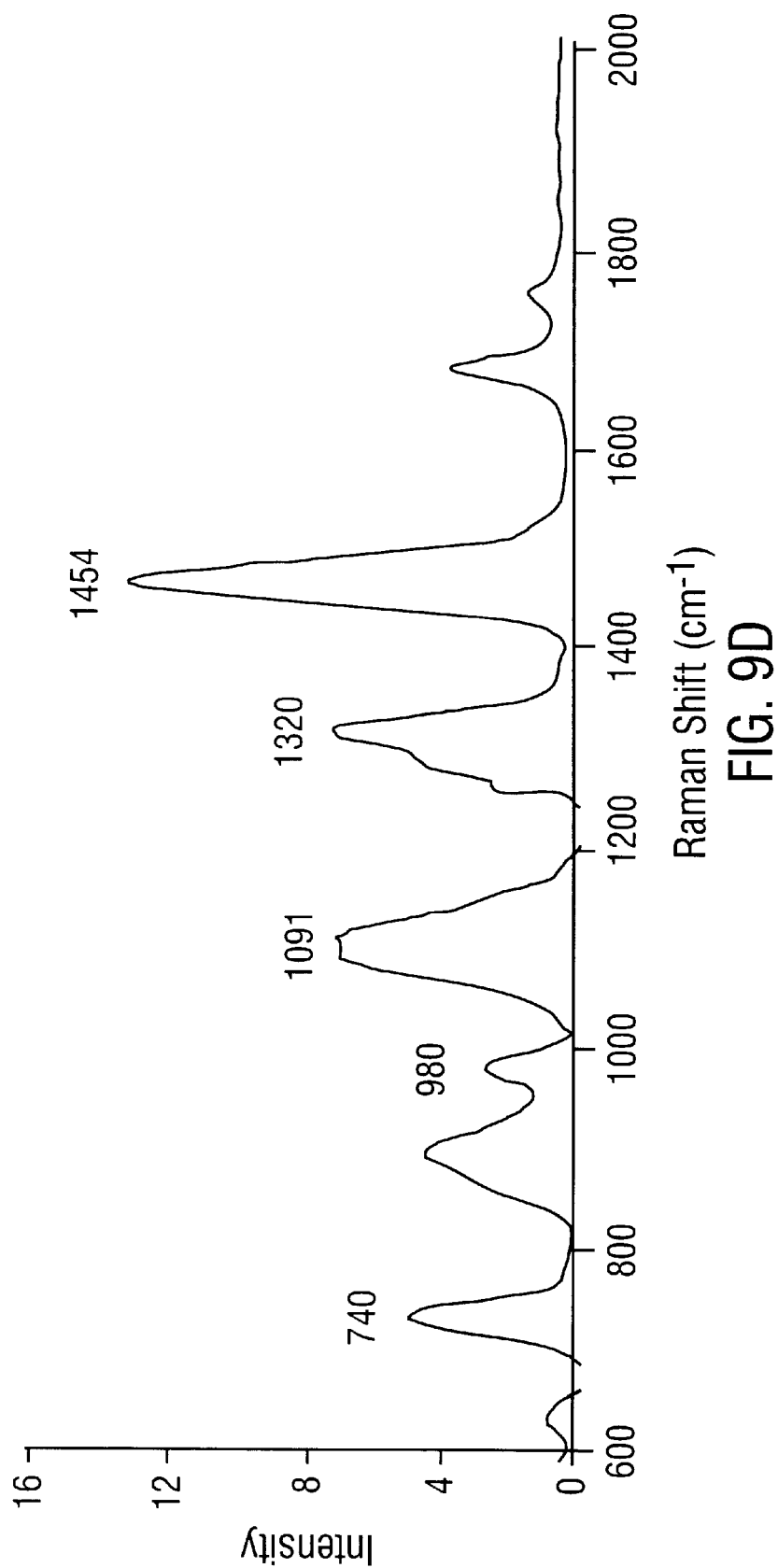

Raman spectra were measured from potential chromophores that were most likely to contribute to the spectral signature of tissue, including collagen, elastin, glucose, glucose 1-phosphate, glycogen, hemoglobin, DNA and RNA, tryptophan, tyrosine and various phospholipids. Of these, the primary contributors to the peaks observed in tissue, appear to be collagen, glucose 1-phosphate, nucleic acids and various phospholipids. FIG. 9A shows the Raman spectrum measured for collagen, where several peaks overlap with those observed in tissue, including those at 770, 826, 1066, 1181, 1248, 1452 and 1660 $cm^{-1}$ (FIG. 9A). Glucose 1-phosphate is an intermediate product in the glycogen-glucose conversion cycle and found in abundance in cervical epithelial cells. The spectrum of glucose 1-phosphate is shown in FIG. 9B. Peaks observed in glucose 1-phosphate that potentially contribute to tissue spectra are those at 850, 970, 1053, 1091, 1146 and 1350 $cm^{-1}$. The Raman spectra of nucleic acids, shown in FIG. 9C, contain a principle peak at 1320 $cm^{-1}$ observed in tissue Raman spectra. Other peaks that are also present in tissue include those at 770 and 1052 $cm^{-1}$. FIG. 9D shows the Raman spectrum of one major phospholipid—phosphatidylcholine. Potentially contributing peaks include those at 740, 980, 1091, 1320 and 1454 $cm^{-1}$. Other contributing chromophores may include tryptophan (757, 867 $cm^{-1}$) and tyrosine (831, 1182, 1202 $cm^{-1}$). Table 5 summarizes the primary peaks observed in cervical tissue spectra and identifies potential vibrational modes responsible for each peak (M. F. Mitchell, Consult Obstet Gynecol, 6, 70 (1994); R. Manoharan, Y. Wang, R. R. Dasari, S. Singer, R. P. Rava. M. S. Feld, Lasers in Life Sciences, 6, 217 (1995); P. L. Altman, D. D. Katz, Cell Biology, (Federation of American Societies for Experimental Biology, Bethesda, Md., 1976); L Stryer, Biochemistry, (W. H. Freeman & Co., New York, 1988): J. F. Brennan T. J. Romer, A. M. Tercyak, Y. Wang, M. Fitzmaurice, R. S. Lees, J. R. Kramer, R. R. Dasari, M. S. Feld, SPIE, 2388, 105 (1995), which are all hereby incorporated by reference, and also suggests potential tissue bio-molecules associated with the vibrational modes based on the chromophore spectra described as well as the findings of other groups.

TABLE V

Peaks observed in cervical Raman spectra and their associated vibrational modes and contributing molecules.

| Peak Location ($cm^{-1}$) | Intensity of SIL w.r.t normal tissue | Potential Vibrational Mode Assignment | Molecular Assignment based on other work | Molecular Assignment based on this study |
|---|---|---|---|---|
| 626 | ↓ |  |  | silica, glucose 1-phosphate |
| 818 | ↑ | ring 'breathing' | blood | silica, collagen |
| 978 | ↓ | phosphate ion stretching, | phosphorylated proteins, nucleic acid bases | glucose 1-phosphate, phospholipids |
| 1070 | ↓ | phosphate ion stretching |  | glucose 1-phosphate, phospholipids collagen, nucleic acids |
| 1246 | ↓ | amide III | amide proteins | collagen, elastin |
| 1330 | ↑ | ring vibrations in-plane C—H deformations | tryptophan pyridines, adenine, guanine guanine nucleic acids | nucleic acids |
| 1454 | ↓ | $CH_2$—$CH_3$ bending | collagen, elastin guanine, adenine, pyridines | phospholipids, collagen |
| 1656 | ↓ | amide $I^1$ | amide proteins collagen, elastin | collagen, elastin |

EXAMPLE: SPECIFICITY AND SENSITIVITY

Summarized from: Albert A., Harris E. K.: *Multivariate Interpretation of Clinical Laboratory Data*, Marcel Dekker Inc., New York, pp. 75–82, (1987), the disclosure of which is expressly incorporated herein by reference.

Assuming a group of T samples which can be categorized as normal (N samples) or diseased (D samples). A diagnostic test, designed to determine whether the sample is normal or diseased, is applied to each sample. The results of the tests is the continuous variable x, which is then used to determine the sample type. FIG. 22 illustrates a hypothetical distribution of test values for each sample type. A diagnostic method based on this test can easily be defined by choosing a cutoff point, d, such that a sample with an observed value x<d is diagnosed as normal and a sample with an observed value x≧d is diagnosed as abnormal.

Several quantitative measures have been defined to 'evaluate' the performance of this type of method. The first type evaluates the test itself (i.e. measures the ability of the test to separate the two populations, N and D). Sensitivity and specificity are two such measures. The second type is designed to aid in the interpretation of a particular test result (i.e. deciding whether the individual test measurement has come from a normal or diseased sample). Positive and negative predictive value are two measures of this type.

To define these measures, some terminology and notation must be introduced. Referring to Table 6, a sample to be tested can be either normal or diseased; the result of the test for each type of sample can be either negative or positive. True negatives represent those normal with a positive test result. In these cases, the diagnosis based on the rest result is correct. False positives are those normal samples which have a positive test result and false negatives are those diseased samples which have a negative test result. In these cases, the diagnosis based on the test result is incorrect.

TABLE 6

|  | Normal | Diseased | Total Samples |
|---|---|---|---|
| Test Negative ($x < d$) | True Negatives (TN) | False Negatives (FN) | Negatives (Neg) |
| Test Positive ($x \geq d$) | False Positives (FP) | True Positives (TP) | Positives (Pos) |
| Total Samples | N | D | T |

With this terminology, Table 7 contains a definition of sensitivity and specificity, the two measures which assess the performance of the diagnostic method. Specificity is the proportion of normal samples with a negative test result (proportion of normal samples diagnosed correctly). Sensitivity is the proportion of diseased samples with a positive test result (proportion of diseased samples correctly diagnosed). Specificity represents the area under the normal sample distribution curve to the left of the cut off point while sensitivity represent the area under the diseased sample distribution curve to the right of the cut off point.

TABLE 7

| Test Measure | Meaning | Calculation |
|---|---|---|
| Specificity | Proportion of normal samples with negative test result | $Sp = TN/N$ |
| Sensitivity | Proportion of diseased samples with positive test result | $Se = TP/D$ |

While sensitivity and specificity characterize the performance of a particular method, another set of statistics is required to interpret the laboratory test result for a given specimen. The positive and negative predictive value quantify the meaning of an individual test result (Table 8). The positive predictive value is the probability that if the test result is positive, the sample is diseased. The negative predictive value is the probability that if the test result is negative, the sample is normal. Positive and negative predictive value are calculated from Baye's rule as outlined in. Table 8 contains two equivalent formulas for calculation positive and negative predictive value.

TABLE 8

| Measure | Meaning | Calculation 1 | Calculation 2 |
|---|---|---|---|
| Positive Predictive Value | The probability that, if the test is positive, the sample is diseased | $PV_+ = TP/Pos$ | $PV_+ = DSe/(DSe + N(1-Sp))$ |
| Negative Predictive Value | The probability that, if the test is negative, the sample is normal | $PV_- = TN/Neg$ | $PV_- = NSp/(NSp + D(1-Se))$ |

EXAMPLE: PRINCIPAL COMPONENTS

Algorithm for entire spectrum:

| Spectra # | Sample | Sample Type | PC2 | PC3 | PC6 | PC10 | PC11 | PC22 |
|---|---|---|---|---|---|---|---|---|
| 1 | 205 | Normal | 1.543567 | 6.348307 | −11.5265 | −3.85568 | −0.35106 | 2.074359 |
| 2 | 206 | Normal | 0.675776 | 7.682844 | −3.1951 | −1.88044 | 2.758224 | 1.411211 |
| 3 | 208 | Normal | 3.023087 | 8.267263 | 4.48342 | −2.66354 | 1.1581 | 1.350089 |
| 4 | 210 | Normal | 2.795302 | 7.981375 | −8.48441 | −4.54498 | 0.099619 | 2.612589 |
| 5 | 211 | Normal | 0.584463 | 4.663981 | −7.7627 | −3.60148 | 0.411765 | 2.108621 |
| 6 | 212 | Normal | 1.145271 | 4.260482 | −6.33389 | −1.98227 | 0.475544 | 0.919255 |
| 7 | 214 | Normal | 1.596303 | 4.153986 | −6.00904 | −2.25171 | 0.054386 | 1.753455 |
| 8 | 216 | Normal | 10.24184 | 2.724157 | −8.21057 | −1.598 | 0.794613 | −0.00061 |
| 9 | 218 | Normal | 3.184082 | 9.355728 | −8.06321 | −1.25937 | −0.40054 | 1.947161 |
| 10 | 220 | Normal | −5.27235 | 7.425923 | −9.02191 | −0.50585 | −0.95993 | 2.127007 |
| 11 | 224 | Normal | 3.014144 | 6.76035 | −5.01533 | −2.0569 | −1.50138 | 1.871378 |
| 12 | 226 | Normal | 0.920394 | 10.87519 | 4.232368 | −3.38003 | 0.24081 | 2.185378 |
| 13 | 228 | Normal | 12.53544 | 1.864631 | −8.27384 | −2.42545 | 0.048752 | 1.348167 |
| 14 | 230 | Normal | 2.832068 | 5.122482 | −2.88442 | 0.8595 | −0.18846 | 1.910948 |
| 15 | 234 | Normal | 4.334318 | 4.948299 | −9.9853 | −3.10534 | 5.583419 | 1.500318 |
| 16 | 235 | Normal | 1.524456 | −1.26834 | −3.73109 | −7.37921 | −0.67991 | 2.572718 |
| 17 | 236 | Normal | −1.1622 | −4.14058 | −7.10158 | −5.46803 | 1.238561 | 3.035817 |
| 18 | 238 | Normal | 4.743856 | −0.26435 | −6.10788 | −3.29107 | 1.10041 | 2.248523 |
| 19 | 240 | Normal | 1.776385 | −2.27109 | 4.4548 | 0.072194 | −0.44392 | 3.320742 |
| 20 | 217 | Metaplasia | 1.752317 | 5.937658 | −5.67794 | −1.90016 | 0.085876 | 0.403281 |
| 21 | 219 | Metaplasia | 3.278303 | 3.265713 | −6.14614 | −5.19454 | 3.596982 | 2.192891 |
| 22 | 221 | Inflammation | 4.702379 | 9.837001 | −12.0999 | −2.75127 | −0.9469 | 1.738687 |
| 23 | 222 | Inflammation | 3.296747 | 8.903145 | −2.01524 | −6.28015 | −1.65013 | 1.303856 |
| 24 | 223 | Inflammation | 6.006808 | 9.880243 | −7.69385 | −0.1685 | 3.816562 | 3.699493 |
| 25 | 232 | Inflammation | 0.569056 | 4.714893 | −7.50604 | −6.21167 | 3.826786 | 0.607226 |
| 26 | 207 | Low Grade SIL | 0.561945 | 5.602499 | −4.57135 | −2.37876 | 1.373767 | 0.890093 |
| 27 | 227 | Low Grade SIL | −0.80711 | 5.653207 | −5.48179 | −1.70089 | 2.738444 | 1.496372 |
| 28 | 237 | Low Grade SIL | 2.224185 | −4.41891 | −6.95601 | −1.162 | 0.198199 | 1.485232 |
| 29 | 239 | Low Grade SIL | −2.25774 | −0.10565 | −6.79854 | −0.49424 | −1.33124 | 2.20795 |
| 30 | 209 | High Grade SIL | 2.533221 | 6.647742 | −5.78931 | −2.68879 | 1.717242 | 2.475575 |
| 31 | 213 | High Grade SIL | −0.0895 | 2.906415 | −6.00665 | −2.58069 | 0.035438 | 0.931105 |

-continued

EXAMPLE: PRINCIPAL COMPONENTS

| 32 | 215 | High Grade SIL | −0.7773 | 3.910833 | 4.02586 | 0.626846 | 3.715693 | 2.181627 |
| 33 | 225 | High Grade SIL | 2.272768 | 1.092567 | 4.60775 | 4.32622 | 1.494353 | 0.333735 |
| 34 | 229 | High Grade SIL | −22.5061 | 5.707699 | −8.81068 | −3.32392 | 1.213121 | 1.259896 |
| 35 | 231 | High Grade SIL | 0.676066 | 1.891038 | −2.50145 | −2.54445 | 3.625361 | 2.393629 |
| 36 | 233 | High Grade SIL | −0.45883 | −1.0537 | −3.62572 | 0.717738 | 1.235546 | 0.202693 |

Algorithm for eight intensities:

| Spectra # | Sample # | Sample Type | PC1 | PC2 |
|---|---|---|---|---|
| 1 | 205 | Normal | 1.1458848 | −3.1255965 |
| 2 | 206 | Normal | 1.1901133 | −2.5139951 |
| 3 | 208 | Normal | 1.834169 | −3.0472687 |
| 4 | 210 | Normal | 1.9385339 | −3.0518833 |
| 5 | 211 | Normal | 1.2691274 | −2.3443378 |
| 6 | 212 | Normal | 1.3146177 | −1.9820707 |
| 7 | 214 | Normal | 1.2224279 | −2.204537 |
| 8 | 216 | Normal | 6.8626189 | −2.7992257 |
| 9 | 218 | Normal | 3.2312321 | −4.2633651 |
| 10 | 220 | Normal | 5.0182456 | −1.6072238 |
| 11 | 224 | Normal | 4.9603838 | −2.0805216 |
| 12 | 226 | Normal | 6.2036942 | −2.5109298 |
| 13 | 228 | Normal | 9.2114828 | −2.9830391 |
| 14 | 230 | Normal | 5.2514816 | −2.8088963 |
| 15 | 234 | Normal | 5.9115984 | −2.7809312 |
| 16 | 235 | Normal | 4.1752079 | −1.3949086 |
| 17 | 236 | Normal | 4.3566001 | −0.048286078 |
| 18 | 238 | Normal | 6.693896 | −1.6661062 |
| 19 | 240 | Normal | 4.9669454 | −1.440043 |
| 20 | 217 | Melasia | 4.1113339 | −1.4176762 |
| 21 | 219 | Melasia | 5.3999799 | −1.2857701 |
| 22 | 221 | Inflammation | 5.7796724 | −3.7633856 |
| 23 | 222 | Inflammation | 6.3565578 | −2.4393958 |
| 24 | 223 | Inflammation | 5.7032673 | −2.8104215 |
| 25 | 232 | Inflammation | 3.9806831 | −2.5245282 |
| 26 | 207 | Low Grade SIL | 1.4079334 | −2.4003275 |
| 27 | 227 | Low Grade SIL | 3.5186656 | −1.4919014 |
| 28 | 237 | Low Grade SIL | 4.7394294 | −0.33047979 |
| 29 | 239 | Low Grade SIL | 5.2064229 | −0.94494107 |
| 30 | 209 | High Grade SIL | 2.3771245 | −2.6865663 |
| 31 | 213 | High Grade SIL | 0.70798509 | −1.3977078 |
| 32 | 215 | High Grade SIL | 3.0091378 | −0.80670927 |
| 33 | 225 | High Grade SIL | 4.3683959 | −0.78866125 |
| 34 | 229 | High Grade SIL | 4.0888702 | 0.79444495 |
| 35 | 231 | High Grade SIL | 3.1164238 | −0.86678825 |
| 36 | 233 | High Grade SIL | 3.8430913 | −0.36249117 |

What is claimed is:

1. A method of detecting tissue abnormality in a tissue sample, comprising:
   (i) illuminating said tissue sample with an illumination wavelength of electromagnetic radiation selected to cause said tissue sample to emit a Raman spectrum comprising a plurality of wavelengths shifted from said illumination wavelength;
   (ii) detecting peak intensities of said Raman spectrum wherein said emission wavelengths are shifted about 1070 $cm^{-1}$ and about 1656 $cm^{-1}$ from said illumination wavelength;
   (iii) comparing each of said detected peak intensities at said wavelength shifts with intensities of a Raman spectrum from known normal tissue at corresponding wavelength shifts; and
   (iv) detecting abnormality of said tissue sample, as a function of said comparison, wherein said abnormality detecting step comprises distinguishing precancerous and not precancerous tissue.

2. A method of detecting tissue abnormality in a tissue sample, comprising:
   (i) illuminating said tissue sample with an illumination wavelength of electromagnetic radiation selected to cause said tissue sample to emit a Raman spectrum comprising a plurality of wavelengths shifted from said illumination wavelength;
   (ii) detecting peak intensities of said Raman spectrum wherein said emission wavelengths are shifted about 1330 $cm^{-1}$ and about 1656 $cm^{-1}$ from said illumination wavelength;
   (iii) calculating a ratio of peak intensities; and
   (iv) detecting abnormality of said tissue sample, as a function of said ratio, wherein said abnormality detecting step comprises distinguishing precancerous and not precancerous tissue.

3. A method of detecting tissue abnormality in a tissue sample, comprising:
   (i) illuminating said tissue sample with an illumination wavelength of electromagnetic radiation selected to cause said tissue sample to emit a Raman spectrum comprising a plurality of wavelengths shifted from said illumination wavelength;
   (ii) detecting peak intensities of said Raman spectrum wherein said emission wavelengths are shifted about 1454 $cm^{-1}$ and about 1656 $cm^{-1}$ from said illumination wavelength;
   (iii) calculating a ratio of peak intensities; and (iv) detecting abnormality of said tissue sample, as a function of said ratio, wherein said abnormality detecting step comprises distinguishing low grade precancerous and high grade precancerous tissue.

4. A method of detecting tissue abnormality in a tissue sample, comprising:
   (i) illuminating said tissue sample with an illumination wavelength of electromagnetic radiation selected to cause said tissue sample to emit a Raman spectrum comprising a plurality of wavelengths shifted from said illumination wavelength;
   (ii) detecting a plurality of peak intensities of said Raman spectrum at wavelength shifts selected by their ability to distinguish normal tissue from abnormal tissue;
   (iii) calculating a first ratio between at least two of said plurality of peak intensities of said Raman spectrum; and
   (iv) detecting, as a function of said first ratio, whether the abnormal tissue is SIL or non-SIL.

5. The method of claim 4, further comprising:
   (i) calculating a second ratio between at least two of said plurality of peak intensities of said Raman spectrum; and
   (ii) detecting, as a function of said second ratio, whether the abnormal tissue is high grade SIL or low grade SIL.

* * * * *